(12) United States Patent
Gudmundson et al.

(10) Patent No.: US 8,831,331 B2
(45) Date of Patent: Sep. 9, 2014

(54) METHOD AND SYSTEM FOR PERFORMING X-RAY INSPECTION OF A PRODUCT AT A SECURITY CHECKPOINT USING SIMULATION

(75) Inventors: Dan Gudmundson, Quebec (CA); Eric Bourbeau, Quebec (CA); Luc Perron, Charlesbourg (CA)

(73) Assignee: Optosecurity Inc., Quebec, Quebec (CA)

( * ) Notice: Subject to any disclaimer, the term of this patent is extended or adjusted under 35 U.S.C. 154(b) by 920 days.

(21) Appl. No.: 12/864,988

(22) PCT Filed: Jun. 9, 2009

(86) PCT No.: PCT/CA2009/000811
§ 371 (c)(1),
(2), (4) Date: Jul. 28, 2010

(87) PCT Pub. No.: WO2010/091493
PCT Pub. Date: Aug. 19, 2010

(65) Prior Publication Data
US 2011/0051996 A1 Mar. 3, 2011

Related U.S. Application Data

(60) Provisional application No. 61/151,242, filed on Feb. 10, 2009, provisional application No. 61/182,243, filed on May 29, 2009.

(30) Foreign Application Priority Data

Mar. 27, 2009 (WO) ................ PCT/CA2009/000395
Mar. 27, 2009 (WO) ................ PCT/CA2009/000401

(51) Int. Cl.
*G06K 9/00* (2006.01)
*G01N 9/24* (2006.01)
*G01N 23/10* (2006.01)
*G01N 1/02* (2006.01)

(52) U.S. Cl.
CPC ............ *G01N 9/24* (2013.01); *G01N 2001/024* (2013.01); *G01N 23/10* (2013.01); *G01N 2223/637* (2013.01)
USPC ............ 382/141; 382/154; 382/209; 348/135

(58) Field of Classification Search
CPC .................. G06K 9/3241; G06T 2207/10116; G06T 2207/30112; G06T 2207/10072; G06T 2207/20081; G06T 2207/20221; G06T 7/0097; G01N 2223/637; G01N 23/10; G01N 23/203; G01N 2001/024; G01N 2223/639; G01N 9/24; A61B 19/5295; G01F 23/288
See application file for complete search history.

(56) References Cited

U.S. PATENT DOCUMENTS

| | | | |
|---|---|---|---|
| 3,342,397 A | 9/1967 | Duitsman | |
| 3,589,511 A | 6/1971 | Britt | |
| 3,609,045 A | 9/1971 | Stein | |
| 3,673,394 A | 6/1972 | Hartmann | |
| 4,392,237 A | 7/1983 | Houston | |
| 4,454,949 A | 6/1984 | Flum | |
| 4,497,065 A * | 1/1985 | Tisdale et al. ................. | 382/103 |
| 4,864,142 A | 9/1989 | Gomberg | |
| 4,870,666 A | 9/1989 | Lonn et al. | |
| 4,927,022 A | 5/1990 | Wilson | |
| 4,962,515 A | 10/1990 | Kopans | |
| 4,974,247 A | 11/1990 | Friddell | |
| 4,985,906 A | 1/1991 | Arnold | |
| 5,044,002 A | 8/1991 | Stein | |
| 5,056,124 A | 10/1991 | Kakimoto et al. | |
| 5,400,381 A | 3/1995 | Steude et al. | |
| 5,428,657 A | 6/1995 | Papanicolopoulos et al. | |
| 5,442,672 A | 8/1995 | Bjorkholm et al. | |
| 5,490,218 A | 2/1996 | Krug et al. | |
| 5,557,108 A | 9/1996 | Tumer | |
| 5,568,262 A * | 10/1996 | LaChapelle et al. .......... | 356/627 |
| 5,600,303 A | 2/1997 | Husseiny et al. | |
| 5,600,700 A | 2/1997 | Krug et al. | |
| 5,692,029 A | 11/1997 | Husseiny et al. | |
| 5,768,334 A | 6/1998 | Maitrejean et al. | |
| 5,838,758 A | 11/1998 | Krug et al. | |
| 5,864,600 A | 1/1999 | Gray et al. | |
| 5,974,111 A * | 10/1999 | Krug et al. ..................... | 378/57 |
| 6,018,562 A | 1/2000 | Willson | |

| | | | |
|---|---|---|---|
| 6,026,171 A | 2/2000 | Hiraoglu et al. | |
| 6,041,132 A * | 3/2000 | Isaacs et al. | 382/100 |
| 6,054,712 A | 4/2000 | Komardin et al. | |
| 6,069,936 A | 5/2000 | Bjorkholm | |
| 6,078,642 A * | 6/2000 | Simanovsky et al. | 378/57 |
| 6,175,655 B1 * | 1/2001 | George et al. | 382/257 |
| 6,201,850 B1 | 3/2001 | Heumann | |
| 6,542,574 B2 | 4/2003 | Grodzins | |
| 6,654,445 B2 | 11/2003 | Shepherd et al. | |
| 6,707,381 B1 | 3/2004 | Maloney | |
| 6,707,879 B2 | 3/2004 | McClelland et al. | |
| 6,721,387 B1 | 4/2004 | Naidu et al. | |
| 6,721,391 B2 | 4/2004 | McClelland et al. | |
| 6,753,527 B1 * | 6/2004 | Yamagishi et al. | 250/339.06 |
| 6,763,083 B2 | 7/2004 | Fernandez | |
| H2110 H | 10/2004 | Newman | |
| 6,840,120 B2 | 1/2005 | Sakairi et al. | |
| 6,952,163 B2 | 10/2005 | Huey et al. | |
| 7,033,070 B2 * | 4/2006 | Azami | 374/131 |
| 7,065,175 B2 | 6/2006 | Green | |
| 7,092,485 B2 | 8/2006 | Kravis | |
| 7,149,339 B2 * | 12/2006 | Veneruso | 382/141 |
| 7,154,985 B2 * | 12/2006 | Dobbs et al. | 378/4 |
| 7,164,750 B2 | 1/2007 | Nabors et al. | |
| 7,257,188 B2 | 8/2007 | Bjorkholm | |
| 7,260,254 B2 * | 8/2007 | Highnam et al. | 382/132 |
| 7,274,768 B2 | 9/2007 | Green | |
| 7,317,390 B2 | 1/2008 | Huey et al. | |
| 7,355,402 B1 * | 4/2008 | Taicher et al. | 324/300 |
| 7,386,093 B2 * | 6/2008 | Wu et al. | 378/57 |
| 7,508,908 B2 * | 3/2009 | Hu et al. | 378/54 |
| 7,614,788 B2 | 11/2009 | Gatten | |
| 7,727,567 B2 * | 6/2010 | Heuft | 378/52 |
| 7,787,681 B2 * | 8/2010 | Zhang et al. | 382/128 |
| 7,789,401 B2 | 9/2010 | Ambrefe, Jr. | |
| 7,840,360 B1 * | 11/2010 | Micheels et al. | 702/25 |
| 7,873,201 B2 * | 1/2011 | Eilbert et al. | 382/141 |
| 7,945,017 B2 * | 5/2011 | Chen et al. | 378/57 |
| 8,090,150 B2 * | 1/2012 | Garms | 382/103 |
| 8,116,428 B2 | 2/2012 | Gudmundson et al. | |
| 8,150,105 B2 * | 4/2012 | Mian et al. | 382/104 |
| 8,260,020 B2 * | 9/2012 | Garms | 382/131 |
| 2001/0033636 A1 | 10/2001 | Hartick et al. | |
| 2002/0097833 A1 | 7/2002 | Kaiser et al. | |
| 2003/0062373 A1 | 4/2003 | Holland | |
| 2004/0016271 A1 | 1/2004 | Shah et al. | |
| 2004/0101097 A1 | 5/2004 | Wakayama et al. | |
| 2004/0232092 A1 | 11/2004 | Cash | |
| 2004/0252024 A1 | 12/2004 | Huey et al. | |
| 2005/0036689 A1 | 2/2005 | Mahdavieh | |
| 2005/0058242 A1 | 3/2005 | Peschmann | |
| 2005/0078801 A1 | 4/2005 | Georgeson et al. | |
| 2005/0111618 A1 | 5/2005 | Sommer, Jr. et al. | |
| 2005/0117700 A1 | 6/2005 | Peschmann | |
| 2005/0173284 A1 | 8/2005 | Ambrefe, Jr. | |
| 2005/0193648 A1 | 9/2005 | Klein et al. | |
| 2005/0238232 A1 * | 10/2005 | Ying et al. | 382/170 |
| 2006/0054682 A1 | 3/2006 | de la Huerga | |
| 2006/0078085 A1 | 4/2006 | Zanker | |
| 2006/0086794 A1 | 4/2006 | Knowles et al. | |
| 2006/0115044 A1 | 6/2006 | Wu et al. | |
| 2006/0133566 A1 | 6/2006 | Li et al. | |
| 2006/0187221 A1 | 8/2006 | Lakare et al. | |
| 2006/0193434 A1 | 8/2006 | Green | |
| 2006/0203960 A1 | 9/2006 | Schlomka et al. | |
| 2006/0239402 A1 | 10/2006 | Hu et al. | |
| 2006/0257005 A1 | 11/2006 | Bergeron et al. | |
| 2007/0003009 A1 | 1/2007 | Gray | |
| 2007/0013519 A1 | 1/2007 | Chung et al. | |
| 2007/0041612 A1 | 2/2007 | Perron et al. | |
| 2007/0041613 A1 | 2/2007 | Perron et al. | |
| 2007/0058037 A1 | 3/2007 | Bergeron et al. | |
| 2007/0098142 A1 | 5/2007 | Rothschild et al. | |
| 2007/0132580 A1 | 6/2007 | Ambrefe, Jr. | |
| 2007/0133743 A1 | 6/2007 | Johnson et al. | |
| 2007/0152033 A1 | 7/2007 | Hind et al. | |
| 2007/0192850 A1 | 8/2007 | Cowburn | |
| 2007/0217571 A1 | 9/2007 | Teslyar et al. | |
| 2007/0297560 A1 | 12/2007 | Song et al. | |
| 2008/0056443 A1 | 3/2008 | Hu et al. | |
| 2008/0062262 A1 | 3/2008 | Perron et al. | |
| 2008/0116267 A1 | 5/2008 | Barber | |
| 2008/0138475 A1 | 6/2008 | Heuft | |
| 2008/0152082 A1 | 6/2008 | Bouchard et al. | |
| 2008/0167552 A1 * | 7/2008 | Bouchevreau et al. | 600/431 |
| 2008/0170660 A1 | 7/2008 | Gudmundson et al. | |
| 2008/0181473 A1 * | 7/2008 | Garty et al. | 382/128 |
| 2008/0240578 A1 | 10/2008 | Gudmundson et al. | |
| 2008/0312768 A1 | 12/2008 | Ewing et al. | |
| 2009/0060135 A1 | 3/2009 | Morton | |
| 2009/0146061 A1 | 6/2009 | Manneschi | |
| 2009/0168963 A1 | 7/2009 | Harding | |
| 2009/0196396 A1 | 8/2009 | Doyle et al. | |
| 2009/0252295 A1 | 10/2009 | Foland | |
| 2010/0027741 A1 | 2/2010 | Doyle et al. | |
| 2010/0220910 A1 * | 9/2010 | Kaucic et al. | 382/131 |
| 2010/0284514 A1 * | 11/2010 | Zhang et al. | 378/53 |
| 2011/0007870 A1 | 1/2011 | Roux et al. | |
| 2011/0172972 A1 | 7/2011 | Gudmundson et al. | |
| 2012/0093367 A1 | 4/2012 | Gudmundson et al. | |
| 2012/0275646 A1 | 11/2012 | Drouin et al. | |

FOREIGN PATENT DOCUMENTS

| | | |
|---|---|---|
| CA | 2 574 402 A1 | 1/2006 |
| CA | 2 623 812 A1 | 5/2007 |
| CA | 2 666 838 A1 | 3/2008 |
| CA | 2 676 913 A1 | 3/2008 |
| CA | 2 700 553 C | 4/2011 |
| CA | 2 709 468 C | 6/2011 |
| CA | 2 690 163 C | 8/2011 |
| CA | 2 651 728 C | 4/2012 |
| CA | 2 692 662 C | 6/2012 |
| CA | 2 696 031 C | 8/2012 |
| EP | 2 189 785 A1 | 5/2010 |
| EP | 269196 | 2/2014 |
| EP | 2331944 | 3/2014 |
| EP | 2334565 | 3/2014 |
| GB | 2 420 683 A | 5/2006 |
| GB | 2 441 551 A | 3/2008 |
| JP | 2006-214725 A | 8/2006 |
| WO | 94/12855 A1 | 6/1994 |
| WO | WO98/02763 A1 | 1/1998 |
| WO | 99/45371 A1 | 9/1999 |
| WO | 03/052398 A1 | 6/2003 |
| WO | WO 2004/054329 | 6/2004 |
| WO | 2006/119603 A1 | 11/2006 |
| WO | 2008/009134 A1 | 1/2008 |
| WO | 2008/019473 A1 | 2/2008 |
| WO | 2008/034232 A1 | 3/2008 |
| WO | 2008/036456 A2 | 3/2008 |
| WO | 2008/040119 A1 | 4/2008 |
| WO | 2008/119151 A1 | 10/2008 |
| WO | 2009/024818 A1 | 2/2009 |
| WO | 2009/043145 A1 | 4/2009 |
| WO | 2009/046529 A1 | 4/2009 |
| WO | 2009/114928 A1 | 9/2009 |
| WO | 2009/127353 A1 | 10/2009 |
| WO | 2010/025538 A1 | 3/2010 |
| WO | 2010/025539 A1 | 3/2010 |
| WO | 2010/028474 A1 | 3/2010 |
| WO | 2010/145016 A1 | 12/2010 |

OTHER PUBLICATIONS

Written Opinion of the International Searching Authority; PCT/CA2010/000916.
International Search Report: PCT/CA2010/000916.
International Preliminary Report on Patentability; PCT/CA2008/001591.
Written Opinion of the International Searching Authority; PCT/CA2010/001200.
International Search Report: PCT/CA2010/001200.
International Preliminary Report on Patentability PCT/CA2009/000401.
OA mailed Oct. 6, 2010 in connection with Canadian Patent Appln. 2,696,031.

OA mailed Oct. 29, 2010 in connection with Canadian Patent Appln. 2,651,728.
OA mailed Oct. 28, 2010 in connection with Canadian Patent Appln. 2,676,903.
OA mailed Nov. 2, 2010 in connection with Canadian Patent Appln. 2,690,163.
OA mailed Nov. 17, 2010 in connection with Canadian Patent Appln. 2,709,468.
Examiners Report mailed Jan. 31, 2011 in connection with Canadian Patent Appln. 2,697,525.
USPTO OA mailed Feb. 10, 2011 in connection with U.S. Appl. No. 12/680,622.
USPTO OA mailed Feb. 8, 2011 in connection with U.S. Appl. No. 12/385,253.
USPTO OA mailed Feb. 9, 2011 in connection with U.S. Appl. No. 12/311,522.
USPTO OA mailed Mar. 2, 2011 in connection with U.S. Appl. No. 12/311,031.
Examiners Report mailed Mar. 29, 2011 in connection with Canadian Patent Appln. 2,725,626.
Examiners Report mailed Mar. 29, 2011 in connection with Canadian Patent Appln. 2,690,831.
USPTO OA mailed Apr. 20, 2011 in connection with U.S. Appl. No. 12/311,031.
OA mailed May 2, 2011 in connection with Canadian Patent Appln. 2,692,662.
European Search Report: EP 07 81 5851.
Hewei Gao, et al; "Application of X-ray CT to liquid security inspection: system analysis and beam hardening correction", Nuclear Instruments & Methods in Physics Research, Section A:Accelerators, Spectrometers, Detectors and Associated Equipment, Elsevier, Amsterdam, NL, vol. 579, No. 1, pp. 395-399, Aug. 8, 2007.
EPO communication dated Apr. 11, 2013; Appln. No. 08 876 865.0-1559.
EPO communication dated May 14, 2013; Appln. No. 09 810 945.7-1559.
Pia Dreiseitel, et al; "Detection of liquid explosives using tomosynthetic reconstruction in multiview dual-energy x-ray systems" 1st EU Conference on the Detection of Explosives, held in Avignon, France, from Mar. 14 to 16, 2011; 4 pages.
European Search Report; mailed Feb. 17, 2012; EP 08 83 5738.
European Search Report; mailed Feb. 1, 2012; EP 08 87 6865.
European Search Report; mailed Oct. 7, 2011; EP 09 81 0945.
International Preliminary Report on Patentability issued Oct. 24, 2011; International Patent Application PCT/CA2010/000916; 17 pages.
International Preliminary Report on Patentability issued Nov. 22, 2011; International Patent Application PCT/CA2010/001200; 12 pages.
Examiner's Report mailed Jul. 19, 2011 in connection with Canadian Patent Application 2,651,728—2 pages.
Examiner's Report mailed Jul. 5, 2011 in connection with Canadian Patent Application 2,696,031—2 pages.
Examiner's Report mailed Aug. 10, 2011 in connection with Canadian Patent Application 2,725,626—4 pages.
Examiner's Report mailed Sep. 2, 2011 in connection with Canadian Patent Application 2,737,075—3 pages.
USPTO NOA mailed Sep. 15, 2011 in connection with U.S. Appl. No. 12/311,031.
USPTO NOA mailed May 6, 2011 in connection with U.S. Appl. No. 12/311,522.
USPTO NOA mailed May 5, 2011 in connection with U.S. Appl. No. 12/385,253.
USPTO NOA mailed May 6, 2011 in connection with U.S. Appl. No. 12/680,622.
USPTO OA mailed Sep. 30, 2010 in connection with U.S. Appl. No. 12/311,031.
USPTO OA mailed Aug. 12, 2010 in connection with U.S. Appl. No. 12/311,522.
USPTO OA mailed Aug. 5, 2010 in connection with U.S. Appl. No. 12/385,253.
Canadian OA mailed Aug. 31, 2010 in connection with Canadian Appln. 2,690,831.

Canadian OA mailed Aug. 31, 2010 in connection with Canadian Appln. 2,692,662.
European Search Report mailed Jul. 18, 2012 European Patent Application No. 09839849.8.
Examiner's Report mailed Jul. 18, 2012 European Patent Application No. 09810945.7.
Examiner's Report mailed Aug. 31, 2012 European Patent Application No. EP2007815851.6.
U. Bottigli, et al; "Voxel-based Monte Carlo simulation of X-ray imaging and spectroscopy experiments", Spectrochimia Acta. Part B; Atomic Spectroscopy, vol. 59, No. 10-11 Oct. 8, 2004, pp. 1747-1754; XP004598270.
M. Sluser, et al; "Model-Based Probabilistic Relaxation Segmentation Applied to Threat Detection in Airport X-ray Imagery", Electrical and Computer Engineering, 1999 IEEE Canadian Conference on Edmonton, Alta., Canada, May 9 to May 12, 1999, pp. 720-726, vol. 2, XP032158352.
Examiner's Report mailed on Nov. 7, 2012 in connection with European patent application No. 08876865.0, 3 pages.
Examiner's Report mailed on Jan. 16, 2013 in connection with Canadian patent application No. 2,697,586, 3 pages.
Examiner's Report mailed on Feb. 4, 2013 in connection with Canadian patent application No. 2,677,439, 2 pages.
Non-Final Office Action issued on Mar. 1, 2013 in connection with U.S. Appl. No. 12/681,826, 32 pages.
Non-Final Office Action issued on Feb. 28, 2013 in connection with U.S. Appl. No. 13/063,869, 52 pages.
Restriction Requirement issued on Mar. 11, 2013 in connection with U.S. Appl. No. 12/680,625, 6 pages.
PCT CA2007/001658 ISR Jan. 10, 2008—Optosecurity Inc. et al.
PCT CA2007/001658 Written Opinion Jan. 10, 2008 Optosecurity Inc et al.
PCT CA2007/001658 Informal Communication w/Applicant Sep. 22, 2008.
PCT CA2007/001658 International Preliminary Report on Patentability Dec. 17, 2008.
PCT CA2007/001749 ISR Jan. 14, 2008 Optosecurity Inc. et al.
PCT CA2008/001591 ISR Nov. 20, 2008 Optosecurity Inc et al.
PCT CA2008/001591 Written Opinion Nov. 20, 2008 Optosecurity Inc. et al.
PCT CA2008/001721 ISR Dec. 4, 2008 Optosecurity Inc. et al.
PCT CA2008/001721 Written Opinion Dec. 4, 2008 Optosecurity Inc et al.
PCT CA2008/001792 ISR Dec. 5, 2008 Optosecurity Inc. et al.
PCT CA2008/001792 Written Opinion Dec. 5, 2008 Optosecurity Inc et al.
PCT CA2008/001792 International Preliminary Report on Patentability Feb. 1, 2010 Optosecurity Inc. et al.
PCT CA2008/002025 ISR Jun. 4, 2009 Optosecurity Inc. et al.
PCT CA2008/002025 Written Opinion Jun. 4, 2009 Optosecurity Inc et al.
PCT CA2008/000395 ISR Jul. 6, 2009 Optosecurity Inc. et al.
PCT CA2008/000395 Written Opinion Jul. 6, 2009 Optosecurity Inc. et al.
PCT CA2008/000401 ISR Aug. 6, 2009 Optosecurity Inc. et al.
PCT CA2008/000401 Written Opinion Aug. 6, 2009 Optosecurity Inc. et al.
PCT CA2009/000811 ISR Nov. 10, 2009 Optosecurity Inc. et al.
PCT CA2009/000811 Written Opinion Nov. 10, 2009 Optosecurity Inc. et al.
PCT CA2007/001749 International Preliminary Report on Patentability Apr. 7, 2009 Optosecurity Inc. et al.
PCT CA2007/001749 Written Opinion Jan. 14, 2008 Optosecurity Inc. et al.
PCT CA2008/001721 International Report on Patentability Apr. 15, 2010 Optosecurity Inc. et al.
OA mailed Jul. 29, 2009 in connection with CA Patent Appln. 2,651,728 6 pages.
OA mailed Jul. 10, 2009 in connection with CA Patent Appln. 2,666,838 3 pages.
OA mailed Nov. 3, 2009 in connection with CA Patent Appln. 2,666,838 5 pages.

OA mailed Jan. 28, 2010 in connection with CA Patent Appln. 2,676,913 2 pages.
OA mailed Jan. 28, 2010 in connection with CA Patent Appln. 2,666,838 5 pages.
R. Benjamin; "Object-Based 3D X-Ray Imaging for Second-Line Security Screening", London, 1995 (exact date not given).
Pinpoint TM Threat Identification Software, http://www.guardiantechintl.com/security.php?npage=pinpoint, Jul. 25, 2005, 4 pages.
"Secure Flight Passenger Screening Program", http://www.globalsecurity.org/security/systems/passenger_screen.htm, Oct. 28, 2005, 6 pages.
Optosecurity, "Security Technology Overview: Advanced Vehicle Verification & Threat Identification", 1 page.
Airport Magazine, Solutions, Products, Services, vol. 7, Mar. 2006, 5 pages.
D.L. Page, et al; "Perception-based 3D Triangle Mesh Segmentation Using Fast Marching Watersheds", Proc. Intl. Conf. on Computer Vision and Pattern Recognition, vol. II, pp. 27-32, Madison, WI, Jun. 2003.
Nicolas Freud, et al; "Simulation of X-Ray NDT Imaging Techniques", Proceedings of the 15$^{th}$ World Conference on Non-Destructive Testing, Rome, Oct. 15-21, 2000, http://www.ndt.net/article/wcndt00/papers/idn256/idn256.htm, pages consulted on Dec. 3, 2009, 7 pages.
Wei Xie,et al; "Simulation of X-ray Imaging Systems for Luggage Inspection", Second Explosives Detection Symposium and Aviation Security Conference, Nov. 12-15, 1996, pp. 248-253.
OA mailed Mar. 2, 2010 in connection with CA Patent Appln. 2,676,903 4 pages.
OA mailed May 5, 2010 in connection with CA Patent Appln. 2,676,913 2 pages.
OA mailed May 14, 2010 in connection with CA Patent Appln. 2,690,831 3 pages.
OA mailed Jun. 7, 2010 in connection with CA Patent Appln. 2,692,662 3 pages.
OA mailed Jun. 30, 2010 in connection with CA Patent Appln. 2,696,031 2 pages.
OA mailed Jun. 28, 2010 in connection with CA Patent Appln. 2,697,525 3 pages.
OA mailed Mar. 19, 2010 in connection with CA Patent Appln. 2,651,728 2 pages.
OA mailed Mar. 31, 2010 in connection with CA Patent Appln. 2,690,163 3 pages.
Examiner's Report mailed on May 29, 2013 in connection with European Patent Application No. 09839849.8—6 pages.
Examiner's Report mailed on Jul. 22, 2013 in connection with Canadian Patent Application 2,737,075—3 pages.
Examiner's Report mailed on Jul. 23, 2013 in connection with Canadian Patent Application 2,677,439—2 pages.
USPTO NFOA dated Aug. 14, 2013 in connection with U.S. Appl. No. 12/680,625.
USPTO NFOA dated Sep. 25, 2013 in connection with U.S. Appl. No. 13/313,635.
USPTO FOA dated Nov. 14, 2013 in connection with U.S. Appl. No. 13/063,869.
USPTO NOA mailed Dec. 2, 2013 in connection with U.S. Appl. No. 12/680,625.
Extended European Search Report issued on Dec. 18, 2013 in connection with European patent application No. 13191619.9—6 pages.
Xiang Li et al., "A numerical simulator in VC++ on PC for iterative image reconstruction", Journal of X-ray Science and Technology, vol. 1, No. 2, Jan. 1, 2003, pp. 61-70, XP055063644, issn: 0895-3996.
USPTO NOA mailed Jan. 16, 2014 in connection with U.S. Appl. No. 13/313,635.
USPTO NOA mailed Mar. 17, 2014 in connection with U.S. Appl. No. 13/387,578.
European Search Report mailed on Apr. 14, 2014 in connection with European Patent Application No. 10788557.6—8 pages.
Notice of Allowance issued on Jan. 16, 2014 in connection with U.S. Appl. No. 13/313,635—10 pages.
Notice of Allowance issued on Mar. 17, 2014 in connection with U.S. Appl. No, 13/387,578—8 pages.

* cited by examiner

*Primary Examiner* — Manav Seth
(74) *Attorney, Agent, or Firm* — Ladas & Parry LLP

(57) ABSTRACT

A method, an apparatus and a system are provided for deriving a characteristic of a product using X-rays. X-ray image data associated with the product is received, the X-ray image data being derived by performing an X-ray scan of the product using an X-ray imaging apparatus and conveying attenuation information resulting from interaction of X-rays with the product. A response of a reference product to X-rays is then simulated to generate simulated X-ray image data. The simulated X-ray image data and the received X-ray image data are then processed to derive one or more characteristics of the product. Information conveying the derived characteristic of the product is then released. In a specific implementation, the product is a liquid product comprised of a bottle at least partially filled with liquid and the derived characteristic of the liquid product is a threat status assessment associated with the liquid in the bottle. In another aspect, a simulation engine for simulating interactions between X-rays and objects is also provided.

53 Claims, 20 Drawing Sheets

METHOD AND SYSTEM FOR PERFORMING X-RAY INSPECTION OF A PRODUCT AT A SECURITY CHECKPOINT USING SIMULATION

CROSS-REFERENCE TO RELATED APPLICATIONS

For the purpose of the United States, the present application claims the benefit of priority under 35 USC §119 based on:
- U.S. provisional patent application Ser. No. 61/151,242 filed on Feb. 10, 2009 by Luc Perron et al. and presently pending.
- PCT International Patent Application serial number PCT/CA2009/000395, entitled "Method and system for performing X-ray inspection of a liquid product at a security check point", filed in the Canadian Receiving Office on Mar. 27, 2009 by Optosecurity Inc. et al. and presently pending.
- PCT International Patent Application Ser. No. PCT/CA2009/000401 entitled "Method and apparatus for assessing properties of liquids by using X-rays", filed in the Canadian Receiving Office on Mar. 27, 2009 by Optosecurity Inc. et al. and presently pending.
- U.S. provisional patent application Ser. No. 61/182,243 filed on May 29, 2009 by Dan Gudmundson et al. and presently pending.

The contents of the above-referenced patent documents are incorporated herein by reference.

FIELD OF THE INVENTION

The present invention relates to technologies for performing inspection of a product using penetrating radiation such as X-rays. The invention has numerous applications; in particular it can be used for scanning bottles holding liquid substances at airport security check points.

BACKGROUND

Some liquids or combinations of liquids and other compounds may cause enough damage to bring down an aircraft. As a result, authorities have implemented a ban of most liquids, gels and aerosols in cabin baggage. The results of such a ban have been disruptions in operations (e.g., a longer screening process; a change of focus for screeners; additional line-ups), major inconveniences for passengers (as well as potential health hazards for some) and economic concerns (e.g., increased screening costs; lost revenues for airlines and duty free shops; large quantities of confiscated—including hazardous—merchandise to dispose of), and so on.

Commercially available X-ray screening systems provide methods for detecting low level bulk explosive. Such methods typically detect explosives by estimating the effective atomic numbers ($Z_{eff}$ values) of the products under inspection from an X-ray image of that product, the x-ray image being generated by a dual energy X-ray machine. Although such methods are generally precise enough for detecting some high density and high $Z_{eff}$ plastics explosives, they are inadequate for assessing the threat status of liquids.

In light of the above, there is a need to provide an improved technology-based solution for performing inspection of products, and in particular for performing inspection of liquid products, that alleviates at least in part the deficiencies of the existing systems.

SUMMARY

In accordance with a broad aspect, the present invention provides a method for assessing a threat status of a liquid product under inspection at a security checkpoint. The liquid product is comprised of a bottle holding a liquid, wherein the bottle is at least partially filled with liquid. The method comprises receiving X-ray image data associated with the liquid product, the X-ray image data being derived by performing an X-ray scan of the liquid product using an X-ray imaging apparatus and conveying attenuation information resulting from interaction of X-rays with the liquid product. The method also comprises simulating a response of a reference liquid product to X-rays to generate simulated X-ray image data and processing the simulated X-ray image data and the received X-ray image data to determine the threat status of the liquid product under inspection. The method further comprises releasing information conveying the determined threat status of the liquid product.

In a specific example of implementation, the reference liquid product is comprised of a reference bottle and a reference liquid. The method comprises deriving a virtual model of the reference liquid product and using the virtual model of the reference liquid product to simulate the response of the reference liquid product to X-rays and generate the simulated X-ray image data.

In a specific example of implementation, deriving the virtual model of the reference liquid product comprises generating a set of candidate virtual models and selecting a virtual model from the set of candidate virtual models at least in part by simulating responses to X-rays of the candidate virtual models and comparing the simulated responses to X-rays to the X-ray image data associated with the liquid product under inspection. In a non-limiting example of implementation, selecting at least one virtual model from the set of candidate virtual models comprises:
a) simulating responses to X-rays of the candidate virtual models in the set of candidate virtual models to obtain simulated X-ray data;
b) effecting a comparison between the simulated X-ray data to the X-ray data associated to the liquid product under inspection;
c) selecting the at least one virtual model from the set of candidate virtual models as the virtual model of the reference liquid product at least in part based on the comparison between the simulated X-ray data and the X-ray data associated to the liquid product under inspection.

In a specific example of implementation, the candidate virtual models are generated in part by deriving geometric information from the X-ray image data associated with the liquid product under inspection. In a non-limiting example of implementation, the set of candidate virtual models generated includes virtual models of bottles having various cross-sectional shapes including for example, bottles having a generally circular shape, a generally elliptical shape, a generally rectangular shape and/or a generally square shape. Optionally, the set of candidate virtual models may also include candidate virtual models associated with different levels of fill. For example, for a given bottle shape, multiple levels of fill may be considered (e.g. 25% full of liquid, 50% full of liquid, 75% full of liquid, 100% full of liquid).

In a specific example of implementation, the set of candidate virtual models includes candidate virtual models associated to different liquid substances from a set of reference liquid substances. In a non-limiting example of implementation, the set of reference liquid substances includes at least one reference liquid substance that constitutes a threat.

In a specific example of implementation, the X-ray image data associated with the liquid product under inspection is derived using a single view X-ray machine.

In an alternative specific example of implementation, the X-ray image data associated with the liquid product under inspection is derived using a multi-view X-ray machine. In such an implementation, the X-ray image data conveys a first X-ray image of the liquid product taken by subjecting the liquid product to X-rays in a first orientation and a second X-ray image of the liquid product taken by subjecting the liquid product to X-rays in a second orientation. The method comprises deriving a virtual model of the reference liquid product based at least in part on the first X-ray image and the second X-ray image and using the virtual model of the reference liquid product in simulating responses of the reference liquid product to X-rays in the first orientation, the second orientation or both the first and the second orientations to generate simulated X-ray image data.

In a non-limiting specific example of implementation, the liquid product is supported by a tray while the liquid product is subjected to an X-ray inspection at a security checkpoint to determine the threat status of the bottle filled with liquid. The bottle has a top extremity and a bottom extremity and the tray is configured to hold the bottle in an inclined position such that a meniscus in the bottle filled with liquid has a tendency to migrate toward one of the extremities of the bottle filled with liquid. Alternatively, the tray may be a conventional tray with a flat bottom surface.

In accordance with another broad aspect, the invention provides a computer readable storage medium storing a program element suitable for execution by a computing apparatus for assessing a threat status of a liquid product under inspection at a security checkpoint, the liquid product being comprised of a bottle holding a liquid, wherein the bottle is at least partially filled with liquid. The computing apparatus comprises a memory unit and a processor operatively connected to the memory unit. The program element, when executing on the processor, is operative for assessing the threat status of a liquid product in accordance with the above-described method.

In accordance with yet another broad aspect, the invention provides an apparatus for assessing a threat status of a liquid product under inspection at a security checkpoint, where the liquid product is comprised of a bottle holding a liquid and wherein the bottle is at least partially filled with liquid. The apparatus comprises an input, a processing unit and an output and is operative for assessing the threat status of a liquid product in accordance with the above-described method.

In accordance with a further broad aspect, the invention provides a system suitable for assessing a threat status of a liquid product under inspection at a security checkpoint. The liquid product is comprised of a bottle holding a liquid, wherein the bottle is at least partially filled with liquid. The system comprises an inspection device for performing an X-ray inspection on the liquid product using penetrating radiation to generate an X-ray image of the liquid product. The system also comprises an apparatus for assessing the threat status of the liquid product. The apparatus comprises an input, a processing unit and an output and is operative for assessing the threat status of a liquid product in accordance with the above-described method. The system further comprises a display screen in communication with the output of the apparatus for visually conveying to an operator the assessed threat status of the liquid product based on information released by the apparatus.

In accordance with another broad aspect, the invention provides an apparatus for assessing a threat status of a liquid product under inspection at a security checkpoint. The liquid product is comprised of a bottle holding a liquid, wherein the bottle is at least partially filled with liquid. The apparatus comprises means for receiving X-ray image data associated with the liquid product, the X-ray image data being derived by performing an X-ray scan of the liquid product using an X-ray imaging apparatus and conveying attenuation information resulting from interaction of X-rays with the liquid product. The apparatus also comprises means for simulating a response of a reference liquid product to X-rays to generate simulated X-ray image data. The apparatus also comprises means for processing the simulated X-ray image data and the received X-ray image data to determine the threat status of the liquid product and means for releasing information conveying the determined threat status of the liquid product.

In accordance with another broad aspect, the invention provides a method for deriving a characteristic of a product using X-rays. The method comprises receiving X-ray image data associated with the product, the X-ray image data being derived by performing an X-ray scan of the product using an X-ray imaging apparatus and conveying attenuation information resulting from interaction of X-rays with the product. The method also comprises simulating a response of a reference product to X-rays to generate simulated X-ray image data and processing the simulated X-ray image data and the received X-ray image data to derive the characteristic of the product. The method further comprises releasing information conveying the derived characteristic of the product.

In specific examples of implementation, the reference product may be comprised of a reference liquid product, a reference solid explosive, a reference substance (e.g. drug) and/or any other type of substance or compound having known characteristics.

In specific example of implementation, the derived characteristic of the product may convey, for example, material density information, material type information, material chemical formula, a threat status, one or more linear attenuation coefficients and/or an effective atomic number ($Z_{eff}$ number) amongst other characteristics. Optionally, a tolerance level may also be associated with the characteristics of the reference product. As a result, the reference product may be associated with a range of values for a given characteristic (e.g. density±Δdensity, Zeff±ΔZeff). In a non-limiting example of implementation, the one or more linear attenuation coefficients include X-ray attenuation coefficients associated to respective portions of the X-ray spectrum. Optionally, the one or more linear attenuation coefficients may also include an average low energy linear attenuation coefficient and an average high energy linear attenuation coefficient.

In a specific example of implementation, the method comprises deriving a virtual model of the reference product and using the virtual model of the reference product in simulating the response of the reference product to X-rays to generate the simulated X-ray image data.

The virtual model of the reference product may be derived in a number of different manners.

In a specific example of implementation, deriving the virtual model of the reference product includes generating a set of candidate virtual models. The candidate virtual models may be generated by processing the X-ray image data associated with the product under inspection to derive geometric information associated with the product and using the derived geometric information associated with the product to generate one or more candidate virtual models. In a specific example of implementation, the candidate virtual models generated include virtual models associated to different substances from a set of reference substances. Once the candidate virtual models are generated, at least one virtual model is selected at least in part by simulating responses to X-rays of the candidate virtual models. In a specific implementation, responses to X-rays of the candidate virtual models are simulated to obtain simulated X-ray data. Following this, a comparison between the simulated X-ray data and the X-ray data associated to the product under inspection is performed. At least one virtual model is then selected as the virtual model of the reference product at least in part based on results of the comparison between the simulated X-ray data and the X-ray data associated to the product under inspection.

In a specific example of implementation, the X-ray image data associated with the liquid product under inspection is derived using a single view X-ray machine.

In an alternative specific example of implementation, the X-ray image data associated with the liquid product under inspection is derived using a multi-view X-ray machine. In such an implementation, the X-ray image data conveys a first X-ray image of the liquid product taken by subjecting the liquid product to X-rays in a first orientation and a second X-ray image of the liquid product taken by subjecting the liquid product to X-rays in a second orientation.

In accordance with another broad aspect, the invention provides a computer readable storage medium storing a program element suitable for execution by a computing apparatus for deriving a characteristic of a product based in part on an X-ray image of the product. The computing apparatus comprises a memory unit and a processor operatively connected to the memory unit. The program element, when executing on the processor, is operative for deriving the characteristic of the product in accordance with the above-described method.

In accordance with yet another broad aspect, the invention provides an apparatus for deriving a characteristic of a product based in part on an X-ray image of the product in accordance with the above-described method.

In accordance with a further broad aspect, the invention provides a system suitable for deriving a characteristic of a product. The system comprises an inspection device for performing an X-ray inspection on the product using penetrating radiation to generate an X-ray image of the product. The system also comprises an apparatus having an input, a processing unit and an output where the processing unit is operative for deriving the characteristic of the liquid product in accordance with the above-described method. The system further comprises a display screen in communication with the output of the apparatus for visually conveying to an operator the derived characteristic of the product based on information released by the apparatus.

In accordance with yet another broad aspect, the invention provides an apparatus for simulating a response of a reference product to X-rays. The apparatus comprises a processor for processing characterization data associated with a reference product to generate simulated X-ray image data associated with the reference product by modelling interactions between X-rays and the reference product.

In accordance with specific examples of implementation, the characterization data may convey different types of information related to the reference product, including for example, but not limited to, shape information, material type information and positioning information for positioning the reference product relative to a source of X-rays.

In accordance with yet another broad aspect, the invention provides a method for simulating a response of a reference product to X-rays. The method comprises processing characterization data associated with a reference product to generate simulated X-ray image data associated with the reference product by modelling interactions between X-rays and the reference product. The method also comprises releasing the simulated X-ray image data.

In accordance with yet another broad aspect, the invention provides a computer readable storage medium storing a program element suitable for execution by a computing apparatus for simulating a response of a reference product to X-rays. The computing apparatus comprises a memory unit and a processor operatively connected to the memory unit. The program element, when executing on the processor, is operative for simulating the response of the reference product to X-rays in accordance with the above-described method.

In accordance with yet another broad aspect, the invention provides an apparatus for simulating a response of a reference product to X-rays. The apparatus comprises a simulation engine for processing characterization data associated with the reference product to model interactions between X-rays and the reference product and generate simulated X-ray data. The characterization data conveys shape information associated with the reference product and material type information associated with the reference product. The apparatus also comprises an output in communication with the simulation engine for releasing the simulated X-ray image data.

In accordance with a specific implementation, the characterization data associated with the reference product is derived at least in part based on geometric information associated with a real product. In a non-limiting example, the characterization data associated with the reference product is derived from X-ray image data associated with the real product. The X-ray image data is derived by performing an X-ray scan of the real product using an X-ray imaging apparatus and conveys attenuation information resulting from interaction of X-rays with the real product.

In accordance with a specific implementation, the apparatus comprises a product characterisation module for processing X-ray image data associated to the real product to derive the geometric information associated with the real product and derive the characterization data associated with the reference product based in part on the geometric information associated with the real product.

In accordance with a specific implementation, the apparatus comprises an input for receiving the X-ray image data associated with the real product for processing by the product characterisation module. The X-ray image data is derived by performing an X-ray scan of the real product using an X-ray imaging apparatus and conveys attenuation information resulting from interaction of X-rays with the real product.

In accordance with yet another broad aspect, the invention provides a method for deriving a characteristic of a product. The method comprises processing characterization data associated with the product to generate simulated X-ray image data by modelling interactions between X-rays and the product. The method also comprises processing the simulated X-ray image data to derive the characteristic of the product and releasing data conveying the derived characteristic of the product.

In a specific example of implementation, the characteristic of the product is derived at least in part by comparing the X-ray image data associated with the product to the simulated X-ray image data.

In accordance with another broad aspect, the invention provides an apparatus for deriving a characteristic of a product, the apparatus comprising an input, a processing unit and an output. The apparatus is for deriving a characteristic of a product in accordance with the above described method.

Other aspects and features of the present invention will become apparent to those ordinarily skilled in the art upon review of the following description of specific embodiments of the invention in conjunction with the accompanying Figures.

BRIEF DESCRIPTION OF THE DRAWINGS

A detailed description of examples of implementation of the present invention is provided herein below with reference to the following drawings, in which.

Figure 1:
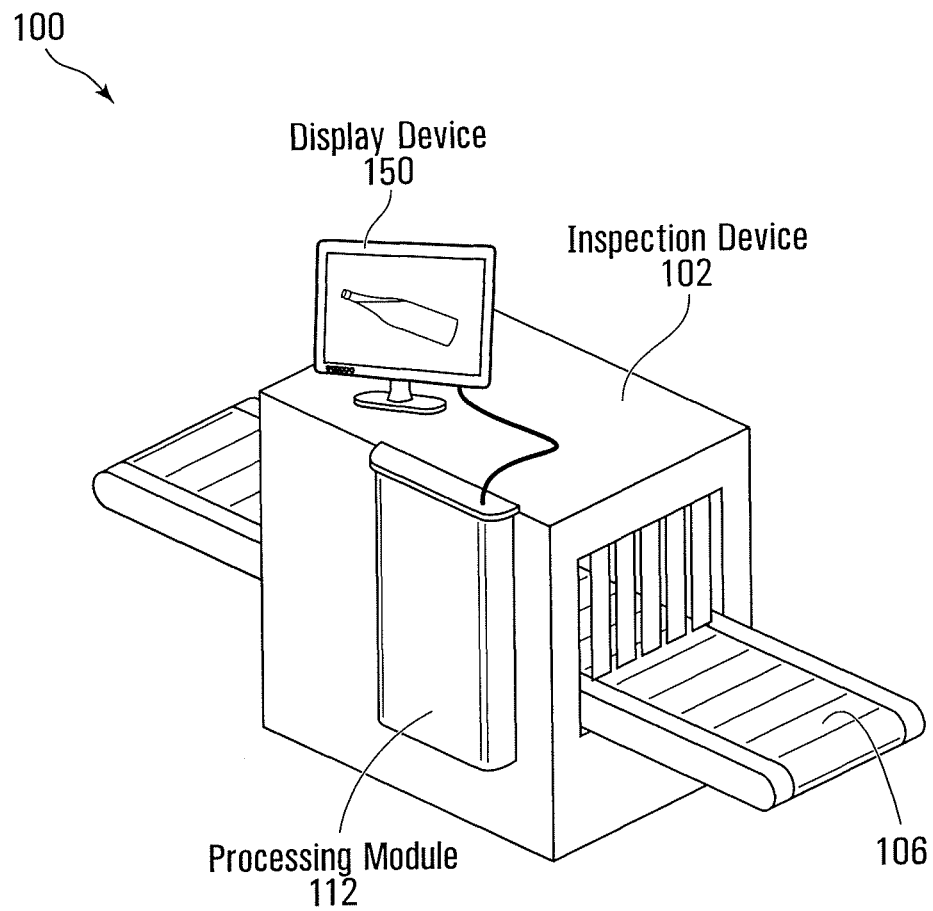
FIG. 1 shows a system for assessing a characteristic of a product at a security checkpoint in accordance with a specific example of implementation of the invention.

In the drawings, embodiments of the invention are illustrated by way of example. It is to be expressly understood that the description and drawings are only for purposes of illustration and as an aid to understanding, and are not intended to be a definition of the limits of the invention.

DETAILED DESCRIPTION

For the purpose of the present description, a "bottle holding a liquid" refers to the combination of a body of liquid and the container in which the liquid is contained. For the purposes of this specification, "liquid" refers to a state of matter that is neither gas nor solid, that generally takes the shape of the container in which it is put and has a characteristic readiness to flow. Heterogeneous liquids would also be encompassed by such a definition.

In addition, a "bottle" refers to the container in which the liquid is contained. Although the term "bottle" typically refers to a cylindrical container that is used to contain liquids (namely beverages), a bottle in this specification refers to any enclosing structure that is made from a material that is suitable to hold the liquid contained within. Such containers include but are not limited to rigid containers, such as a glass bottle or metal (e.g. Aluminum) containers, as well as semi-rigid containers, such as a bottle made of polyvinyl chloride (PVC), polyethylene or of similar flexible materials. The bottle may be of any shape including generally cylindrical bottles, such as those used for beverages (e.g. a wine bottle or a can of a soft drink), square bottles used for beverage and non-beverage liquids (e.g. a carton of milk or fruit juice), elliptical bottles and/or rectangular bottles, as well as bottles of any other suitable shapes. Each bottle has a transverse dimension and a longitudinal dimension that defines an overall size suitable to be carried in hand-carried luggage that is allowed onboard a commercial aircraft. In the case of cylindrical bottles, the transverse dimension is defined by the diameter of the bottle, which may differ between a bottom end and a tapered top end of the bottle. For example, bottles containing wine traditionally have a larger circumference at their bottom end that narrows as the bottle tapers at the top end. Without intent of being bound by any specific definition, bottles filled with liquid of an overall size suitable for transport in hand-carried luggage allowed onboard a commercial aircraft are those that have a transverse dimension that is less than 5 inches, preferably less than 4 inches, and most preferably less than 3 inches. However, these dimensions are merely guidelines and may vary depending on the rules and regulations enforced for such articles by local, national and international transportation organizations.

Specific examples of implementation of the invention will now be described with reference to the figures.

Shown in FIG. 1 is a screening system 100 suitable for deriving one or more characteristics of a product under inspection at a security checkpoint in accordance with a specific example of implementation of the present invention.

For the purpose of simplicity, the present description will focus on an embodiment of the invention in which the product under inspection is a liquid product comprised of a bottle at least partially filled with liquid and the one or more characteristics derived by the system 100 include a threat status associated with the liquid product. It will be appreciated that alternative embodiments of the invention may be configured to determine other characteristics of liquid products. For example, alternative embodiments of the invention may be configured to derive material density information, material type information, material chemical formula, one or more linear attenuation coefficients and/or effective atomic number ($Z_{eff}$ number) from an X-ray image associated with the liquid product under inspection. It will also be appreciated that alternative embodiments of the invention may be configured to determine characteristics of products other than liquid products. For example, alternative embodiments of the invention may be configured to detect the presence of solid explosives, drug substances or other non-liquid substances by deriving characteristics of the product under inspection, such as material density information, material type information, material chemical formula, one or more linear attenuation coefficients and/or effective atomic number ($Z_{eff}$ number). Such alternative embodiments will become apparent to the person skilled in the art in light of the present description.

As depicted, the system 100 includes an inspection device 102 for scanning objects, a processing, module 112 for processing data generated by the inspection device 102 and a display device 150 for visually conveying information to a security operator, the information being derived by the processing module 112 and pertaining to the products/objects being scanned by the inspection device 102.

The inspection device 102 scans a liquid product using penetrating radiation to generate X-ray data conveying an X-ray image of the liquid product. The X-ray image data conveys attenuation information resulting from interaction of X-rays with the liquid product. The processing module 112 receives the X-ray data from the inspection device 102 and processes that data to derive information related to the threat status of that liquid product.

More specifically, the processing, module 112 derives characteristics associated with the liquid product under inspection by simulating a response of a reference liquid product to X-rays. A purpose of the simulation is to be able to predict output intensity of the X-ray inspection device 102 (shown in FIG. 1) at high and low energies based on some level of knowledge (or assumption) of the chemical formula, density and optical path length of the reference product. The reference product is associated with known characteristics based on which simulated X-ray image data is generated. In a non-limiting example, the simulated X-ray image data is compared with the "real" X-ray image data and the result of the comparison is used to confirm and/or infer the nature of the liquid product under inspection. Specific examples of approaches for simulating responses of products to X-rays and for deriving characteristics associated with the liquid product based on simulated responses, including determining the threat status of the liquid product, will be described later on in the specification.

Once characteristics associated with the liquid product have been determined, the processing module 112 releases information conveying these characteristics to a security operator. The display device 150, shown in the figure as a display screen, visually conveys to an operator the determined characteristics of the liquid product, including the threat status of the liquid product, based on the information released by the processing module 112.

Advantageously, the system 100 can provides assistance to human security personnel in assessing the threat status of a liquid product, including full bottles and partially filled bottles, during security screening.

The components of the system 100 depicted in FIG. 1 will now be described in greater detail.

Display Device 150

The display device 150 may be any device suitable for visually conveying information to a user of the system 100. The display device 150 may be part of a computing station, as shown in FIG. 1, may be part of a centralized security station and located remotely from the inspection device 102 or may be integrated into a hand-held portable device (not shown) for example. In another specific example of implementation, the display device 150 includes a printer adapted for displaying in printed format information related to the determined threat status of the liquid product under inspection. The person skilled in the art will readily appreciate, in light of the present specification, that other suitable types of output devices may be used.

In a specific example of implementation, the display device 150 displays to a user of the system 100 a graphical user interface conveying the determined characteristic(s) of the liquid product, including for example the determined threat status of the liquid product, based on the information released by the processing module 112. The graphical user interface (GUI) may also provide functionality for permitting interaction with a user.

The specific manner in which the information is visually conveyed to a human operator may vary from one implementation to the other.

In a first example of implementation, the information conveying the determined threat status of the liquid product conveys the threat status in terms of a level of threat. The level of threat may be represented as alpha-numeric characters (e.g. SAFE/UNSAFE/UNKNOWN), a color indicator (e.g. RED for unsafe; GREEN for safe and YELLOW for UNKNOWN) and/or using any other suitable manner of conveying a level of threat.

In a second example of implementation, the information conveying the determined threat status of the liquid product provides information as to the nature of the liquid product being screened. For example, the GUI may indicate that the liquid product may be water, orange juice, hydrogen peroxide and so on. Optionally, when indicating the nature of the liquid product, a level of confidence in the determination may be displayed. For example, the GUI may indicate that the liquid product is likely to be water with a level of confidence of 80%.

It will be readily apparent to the person skilled in the art that other types of information may be displayed by display device and that the examples provide above have been provided here for the purpose of illustration only.

Inspection Device 102

In a specific example of implementation, the inspection device 102 is in the form of an X-ray machine typical of the type of device used to scan luggage at security checkpoints within airports and other locations. The X-ray machine may be a single view X-ray machine or a multi-view X-ray machine. For the purpose of simplicity, the present description will primarily focus on implementations in which the X-ray machine is of a single-view type. Variants of the invention taking advantage of the multiple X-ray images generated by multi-view X-ray machines will also be presented.

The inspection device 102 will now be described in greater detail with reference to FIG. 2. As depicted, the inspection device 102 includes a scanning area 104, a conveyor belt 106, an X-ray source 108 and an array of X-ray detectors 110. The inspection device 102 performs an X-ray inspection on a liquid product using penetrating radiation in the form of X-rays to generate X-ray image data associated with the liquid product.

The scanning area 104 (also referred to as a scanning tunnel) is defined by an enclosed void between the X-ray source 108 and the array of X-ray detectors 110, in which the objects to be scanned are subjected to penetrating radiation, such as X-rays. The scanning area 104 is typically horizontally oriented and is dimensioned both vertically and horizontally to accommodate the types of objects to be scanned, including articles of hand-carried luggage allowed onboard a commercial aircraft, such as handbags, backpacks, briefcases and shopping bags, among others. The scanning area 104 is centrally traversed by a conveyor belt 106 that is used to convey objects to be scanned both into and out of the scanning area 104 and is described below.

The objects to be scanned can be placed either directly on the conveyor belt 106 or in one or more trays that are then placed on the conveyor belt 106.

The conveyor belt 106 is a horizontally-oriented continuous belt of material arranged in an endless loop between two terminal rollers. The belt 106 has an exterior surface on which objects or trays containing the objects to be scanned are placed, as well as an interior surface within which the terminal rollers (as well as other guide rollers and/or supports) lie.

The width of the conveyor belt 106 is sufficient to accommodate the placement of trays within which the objects to be scanned are placed, while its overall length is sufficient to create an endless loop whose length includes:
- A pre-scanning area that lies before the scanning area 104, where the objects to be scanned are placed on the belt 106;
- The scanning area 104, where the objects being scanned are subjected to penetrating radiation (i.e. X-rays); and
- A post-scanning area that lies after the scanning area 104, where the objects that have been scanned emerge after being subjected to penetrating radiation. It is in that area that a user can pick up his or her objects after the security screening operation is completed.

It is worth noting that the terminal rollers constituting the end points of the conveyor belt 106 at the pre-scanning and post-scanning areas may be connected to motors (not shown) that allow an operator to move the belt 106 forwards or backwards to displace the objects to be scanned between different areas of the X-ray inspection device 102.

The X-ray source 108 is the source of penetrating radiation (in this case, X-ray radiation). The X-ray source 108 is located opposite to the array of X-ray detectors 110 so that X-rays emitted by the source 108 pass through the objects that are located on the conveyor belt 106 and are detected by the array of X-ray detectors 110 as a result. In a non-limiting example, the inspection device 102 is a dual-energy X-ray scanner and the X-ray source 108 emits X-rays at two distinct photon energy levels, either simultaneously or in sequence. Example energy levels include 50 keV (50 thousand electron-volts) and 150 keV, although persons skilled in the art will appreciate that other energy levels are possible.

The array of X-ray detectors 110 detects the penetrating radiation (such as X-rays) that was emitted by the X-ray source 108 and that penetrated the objects to be scanned. The array of X-ray detectors 110 is located opposite to the X-ray source 108 so that X-rays that are emitted by the source 108 pass through the objects that are located on the conveyor belt 106 and are detected by the array 110.

Figure 5:
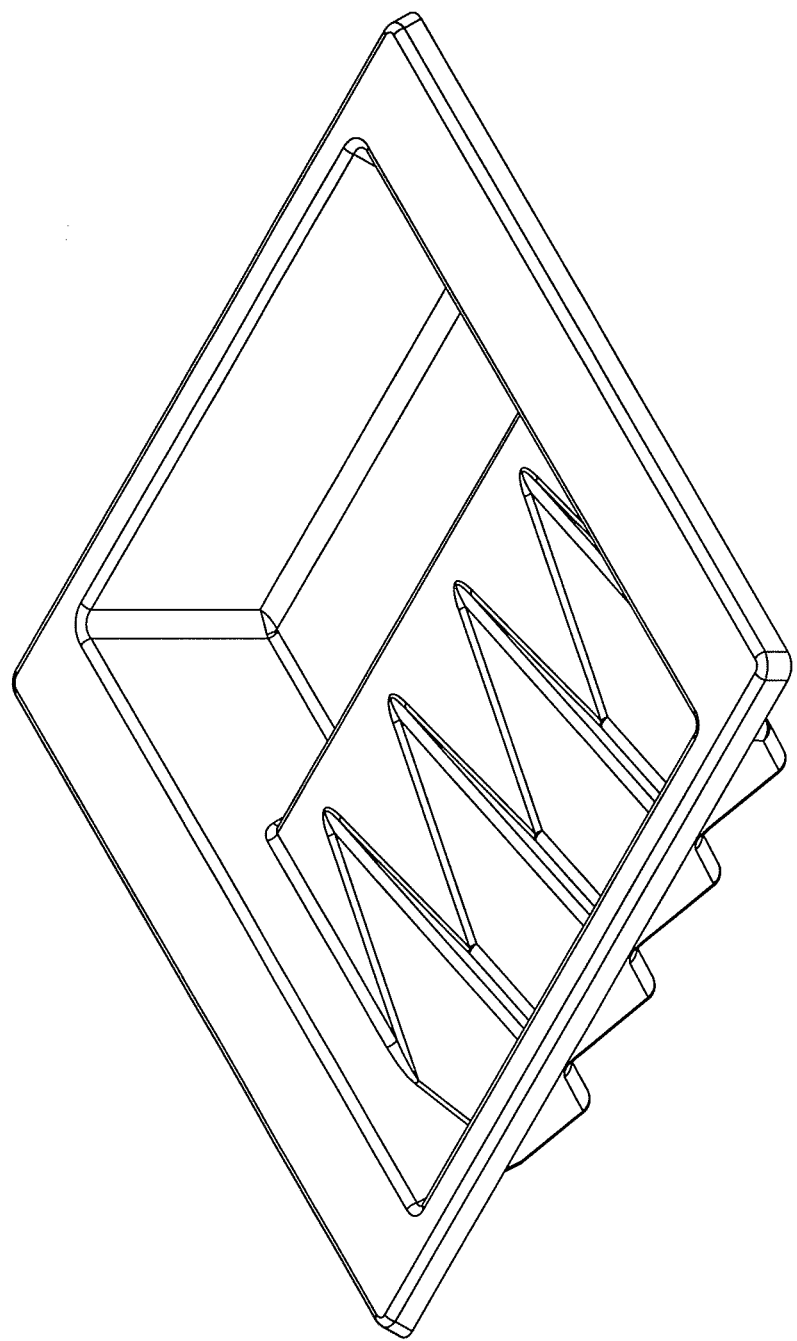
FIG. 5 is a top perspective view of a tray for positioning a bottle in an inclined position during X-ray inspection according to a non-limiting example of implementation of the invention.

In a non-limiting example of implementation, liquid products that are to be inspected are positioned at a known angle (e.g. by means of a tray having an inclined bottom surface) while being scanned by the inspection device 102. By setting a bottle filled with liquid in an inclined position, the meniscus will tend to migrate toward one of the extremities of the bottle. In a specific and non-limiting example of implementation, the liquid products are inclined at a 15° angle from the horizontal plane. It can be appreciated that, in other specific examples of implementation, the angle of incline relative to the horizontal plane can be in the range from about 5° to about 30° and preferably in the range from about 10° to about 20°. In a further specific and non-limiting example of implementation, the angle of incline is in the range from about 10° to about 15°. This may be achieved through the use of a tray having an included bottom surface, of the type depicted in FIG. 5, for example. For specific examples of trays allowing positioning liquids products in inclined positions during screening, the reader is invited to refer to PCT International Patent Application serial number PCT/CA2008/002025 filed in the Canadian Receiving Office on Nov. 17, 2008 by Michel Roux et al. and presently pending. The contents of the aforementioned documents are incorporated herein by reference.

It is to be appreciated that, in alternative examples of implementation, the liquid products under inspection may be positioned in any orientation and any angle, including being positioned in a substantially horizontal plane, while being scanned by the inspection device 102.

It is to be appreciated that, in yet other alternative examples of implementation, the liquid products under inspection may be positioned within a piece of luggage while being scanned by the inspection device 102.

Processing Module 112

The processing module 112 is in communication with the inspection device 102 and receives the X-ray image data output by the array of X-ray detectors 110. In the example depicted in FIGS. 1 and 2, the processing module 112 is shown as a component external to the inspection device 102. It will be appreciated that, in alternate example of implementation of the system 100, the functionality of processing module 112 may be integrated within the inspection device 102.

The processing module 112 uses the X-ray image data output generated by the array of X-ray detectors 110 of the inspection device 102 to generate an X-ray image of the contents being scanned. The X-ray image data can be processed and/or analyzed further using automated means, as will be shown below.

Figure 3:
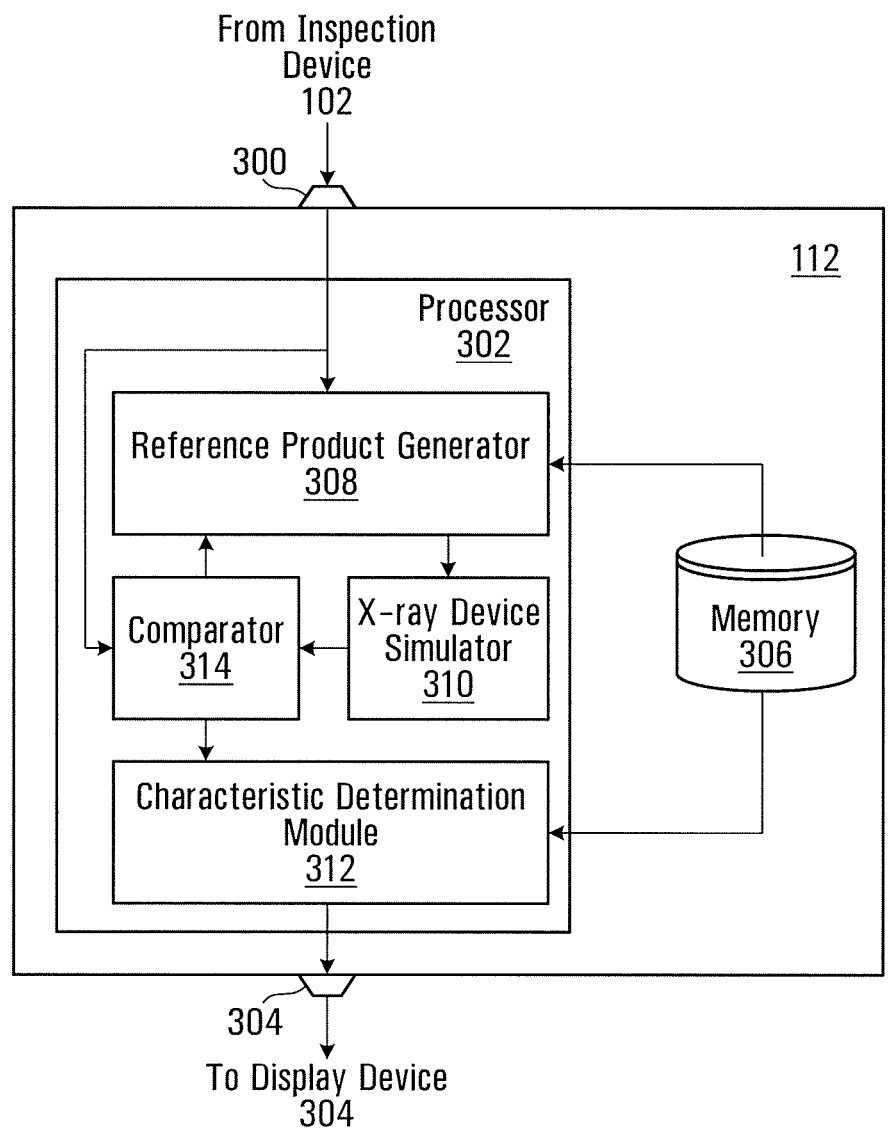
FIG. 3 is a block diagram of a processing module for assessing a characteristic of a product suitable for use in the system depicted in FIG. 1 in accordance with a specific example of implementation of the invention.

A specific example of implementation of the processing module 112 is depicted in FIG. 3 of the drawings.

As shown, the processing module 112 includes an input 300 in communication with the inspection device 102 for receiving there from X-ray image data, a processor 302 in communication with the input 300, a memory 306 storing data for use by the processor 302 and an output 304 in communication with the display device 150 (shown in FIG. 1) for releasing information derived by the processor 302.

The memory 306 may include different types of information depending on the specific functionality implemented by the processing module 112. In a non-limiting example of implementation, the memory 306 stores a knowledge database including a plurality of entries associated with respective liquid substances or respective types of liquid substances. Each entry may include, for example, characteristics associated with the respective liquid substance (or type of liquid substance) such as for example, an identification of the liquid substance, a threat status, material density information, material/substance type information, material chemical formula, one or more linear attenuation coefficients and/or an effective atomic number ($Z_{eff}$ number). In a non-limiting example of implementation, the one or more linear attenuation coefficients includes X-ray attenuation coefficients associated to respective portions of the X-ray spectrum. Optionally, the one or more linear attenuation coefficients may also include an average low energy linear attenuation coefficient and an average high energy linear attenuation coefficient. Optionally still, a tolerance level may be associated with one or more of the characteristics of the liquid substance. For instance the material density information associated with the liquid substance may be expressed as a range of densities such as density±Δdensity and the effective atomic number may be expressed as a range of effective atomic numbers Zeff±ΔZeff.

The processor 302 implements a process for determining one or more characteristics of a liquid product based on the X-ray data received at input 300 from the inspection device 102. In a specific implementation, the one or more characteristics include a threat status. Results obtained by the processor 302 are then released at output 304. Amongst other functionality, the processor 302 simulates responses of reference liquid products to X-rays to derive simulated X-ray image data. The simulated X-ray image data is then used to determine one or more characteristics of the liquid product under inspection, including for example the threat status of the liquid product under inspection.

In the specific example of implementation shown in FIG. 3, the processor 302 includes a number of sub-components namely a reference product generator module 308, an x-ray device simulator 310, an X-ray data comparator device 314 and a characteristic determination module 312.

The reference product generator module 308 receives X-ray image data from the inspection device 102 (shown in FIG. 1), referred to as the "real" X-ray image data, which is associated with the liquid product under inspection, also referred to as the "real" product. The reference product generator module 308 processes the real X-ray image data to derive geometric information associated with the liquid product under inspection. The geometric information is then used to derive characterization data for a reference product. The characterization data of the reference product may convey, amongst others, shape information associated with the reference product, liquid substance content (or liquid substance type) and positioning information for positioning the reference product relative to a source of X-rays and X-ray detectors. Optionally, the reference product generator module 308 receives information from the X-ray data comparator device 314. In a specific example of implementation, the reference product generator module 308 makes use of the result of a comparison between the X-ray image data from the inspection device 102 and simulated X-ray image data generated by the X-ray device simulator 310 to derive a new reference product having new characterization data.

The X-ray device simulator 310 processes characterization data associated with the reference product (generated by the reference product generator module 308) to generate simulated X-ray data by modelling interactions between X-rays and the reference product. The X-ray device simulator 310 releases the simulated X-ray image data to the X-ray data comparator device 314. A specific example of implementation of the X-ray device simulator 310 will be described later on in the specification.

The X-ray data comparator device 314 receives the simulated X-ray image data generated by the X-ray device simulator 310 and compares it to the "real" X-ray image data received at input 300. In a non-limiting example of implementation, the simulated X-ray image data and the "real" X-ray image data each convey attenuation information in the form of a two-dimensional X-ray image. In this non-limiting example of implementation, the comparator device 314 generates an error map conveying differences in attenuation between the "real" X-ray image data and the simulated X-ray image data. As will be appreciated by the person skilled in the art, the magnitude as well as the distribution of the differences in attenuation between the "real" X-ray image data and the simulated X-ray image data provides an indication as to how closely the characterization data of the reference liquid product approximates that of the liquid product under inspection.

For example, differences in attenuation between the "real" X-ray image data and the simulated X-ray image data of a low magnitude and relatively uniform distribution tend to indicate that the reference liquid product is a good representation of the liquid product under inspection. In such cases, the results of the comparison performed by the X-ray data comparator device 314 are provided to the characteristic determination module 312 so that they may be used to confirm and/or infer characteristics of the liquid product under inspection.

Conversely, differences in attenuation between the "real" X-ray image data and the simulated X-ray image data of a large magnitude and/or relatively non-uniform distribution tend to indicate that the reference liquid product may be a poor representation of the liquid product under inspection. In a first example of implementation, the results of the comparison performed by the X-ray data comparator device 314 are provided to the reference product generator module 308 so that they may be used to derive new characterization data associated with a new reference product, where the new reference product is an improved representation of the liquid product under inspection. Alternatively, in a second example of implementation, the results of the comparison are provided to the characteristic determination module 312 along with an indication that the reference product is a poor representation of the liquid product under inspection.

The characteristic determination module 312 is in communication with the X-ray data comparator device 314 and the memory 306. The characteristic determination module 312 receives the results of the comparison performed by the X-ray data comparator device 314 and derives one or more characteristics associated with the liquid product under inspection. In cases where the results of the comparison performed by the X-ray data comparator device 314 indicate that the reference liquid product is a good representation of the liquid product under inspection, the characteristic determination module 312 infers the characteristics of the liquid product under inspection from the characterization data of the reference product. As mentioned above, the characterization data of the reference product may convey, amongst others, an estimated liquid substance or liquid substance type held by reference liquid product. The estimated liquid substance or liquid substance type corresponds to an entry in the memory 306, which stores characteristics associated with the liquid substance or liquid substance type such as, but not limited to an identification of the liquid substance, a threat status, density information, chemical formula, material type information, one or more linear attenuation coefficients and/or an effective atomic number ($Z_{eff}$ number). In a specific example of implementation, the characteristic determination module 312 infers the threat status of the liquid product under inspection from the threat status associated with the estimated liquid substance or liquid substance type of the reference product.

Optionally, in cases where the reference liquid product is a poor representation of the liquid product under inspection, as conveyed by the results of the X-ray data comparator device 314, the characteristic determination module 312 can be used to rule out certain characteristics of the liquid product under inspection.

Process Implemented by the System 100

A specific example of a process implemented by the system 100 (shown in FIG. 1) will now be described with reference to FIG. 4A.

As shown, at step 400 an X-ray scan of a liquid product to be screened is performed by the inspection device 102 (shown in FIG. 1) to obtain X-ray image data associated with the liquid product. The X-ray image data conveys attenuation information resulting from interaction of X-rays with the liquid product.

In a first non-limiting example, the liquid product is placed directly on the conveyor belt 106 of the inspection device 102 or is placed on a tray, which is then placed on the conveyor belt 106 of the inspection device 102.

In a second non-limiting example, the liquid product is placed on a tray having an inclined bottom surface and including retaining member for preventing the liquid product from being displaced during inspection. For example, a tray of the type depicted in FIG. 5 may be used for that purpose. In a specific example of implementation, the bottom surface of the tray's longitudinal axis forms an angle to the horizontal plane in the range from about 5° to about 40°, preferably in the range from about 5° to about 30°, and more preferably in the range from about 10° to about 20°. In a specific non-limiting practical implementation, the angle is between about 10° and about 15°.

The person skilled in the art will appreciate that it is desirable to maintain the stability of the liquid product during the scanning operation in order to improve the accuracy of the threat detection process. Should the liquid product be allowed to roll or otherwise move on the surface of the tray or the conveyor belt, (especially when the bottle is of a circular cross-sectional shape, which would promote such movement) the X-ray image may be taken while the bottle is in motion. This motion may produce corrupted X-ray image data that may lead to a false identification (i.e. a non-threatening liquid being assessed as a threat and vice versa) or require that another X-ray image be taken before any analysis can be performed. As such, mechanisms for positioning the liquid product and preventing it from being displaced during inspection may be used when scanning the liquid product. The reader is invited to refer to the following document for examples of mechanisms for positioning a liquid product:

PCT International Patent Application serial number PCT/CA2008/002025 filed in the Canadian Receiving Office on Nov. 17, 2008 by Michel Roux et al. and presently pending.

The contents of the above mentioned document are incorporated herein by reference.

Figure 2:
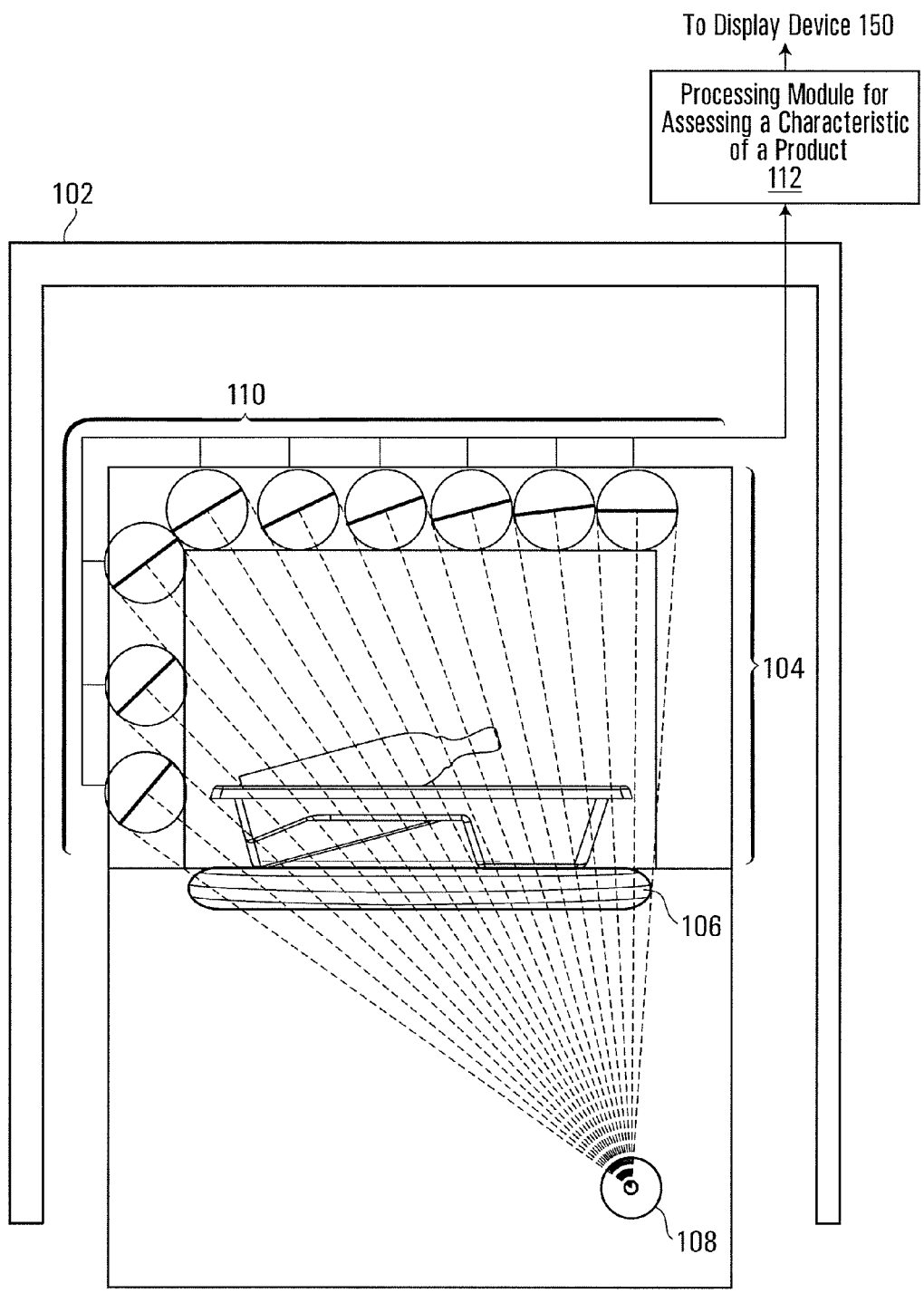
FIG. 2 is a diagrammatic representation of an inspection device suitable for use in the system depicted in FIG. 1 in accordance with a specific example of implementation of the invention.
Figure 6A:
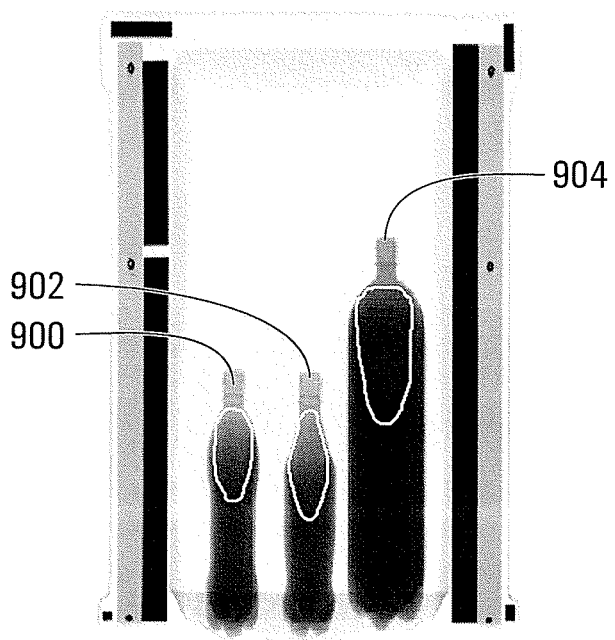
FIG. 6A is an X-ray image of three (3) bottles each at least partially filled with liquid in accordance with a specific example of implementation of the invention.

The liquid product having been placed either directly on the conveyor belt or on a tray is then displaced toward the scanning area 104 of the inspection device 102 (shown in FIG. 2). X-ray image data is then generated by the inspection device 102 by subjecting the liquid product to penetrating radiation. FIG. 6A is an X-ray image of three (3) bottles each at least partially filled with liquid derived from data generated by an inspection device in accordance with a specific example of implementation of the invention. In this figure, the meniscus for each bottle has been emphasized for the purpose of illustration only.

At step 402, the X-ray image data generated by the inspection device 102 is received by the processing module 112 (shown in FIGS. 1 and 3).

At step 404, the processing module 112 processes the X-ray image data to determine one or more characteristics, such as the threat status, of the liquid product scanned at step 400. In a specific implementation, responses of reference liquid products to X-rays are simulated in order to generate simulated X-ray image data. The simulated X-ray image data is then used to confirm and/or infer the characteristics of the liquid product under inspection. Specific examples of the manner in which step 404 may be implemented will be described in greater detail below.

At step 408, the processing module 112 releases information conveying the one or more characteristics determined at step 404, including for example the threat status, of the liquid product under inspection.

Following this, at step 410, the display device 150 (shown in FIG. 1) receives the information released by the processing modules and conveys this information in visual format, and optionally in audio format, to an operator.

Step 404

A specific approach for determining at step 404 one or more characteristics of the liquid product under inspection will now be described with reference to FIGS. 4B, 4C, 4D and 4E. It is to be appreciated that the following example has been provided for the purpose of illustration and that many variations are possible and will become apparent to the person skilled in the art in light of the present application.

Figure 4A:
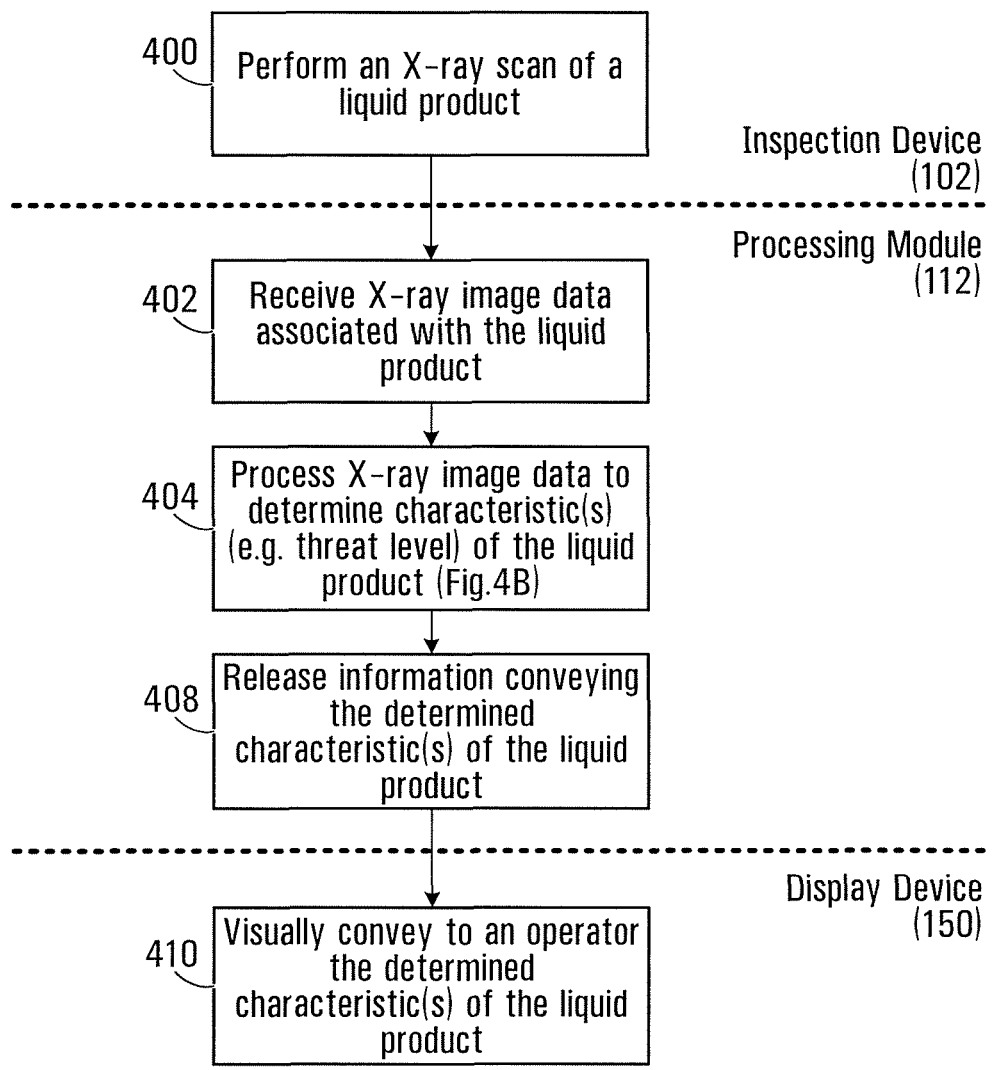
FIGS. 4A, 4B, 4C, 4D and 4E are flow diagrams of a process implemented by the system depicted in FIG. 1 in accordance with a specific example of implementation of the invention.
Figure 4B:
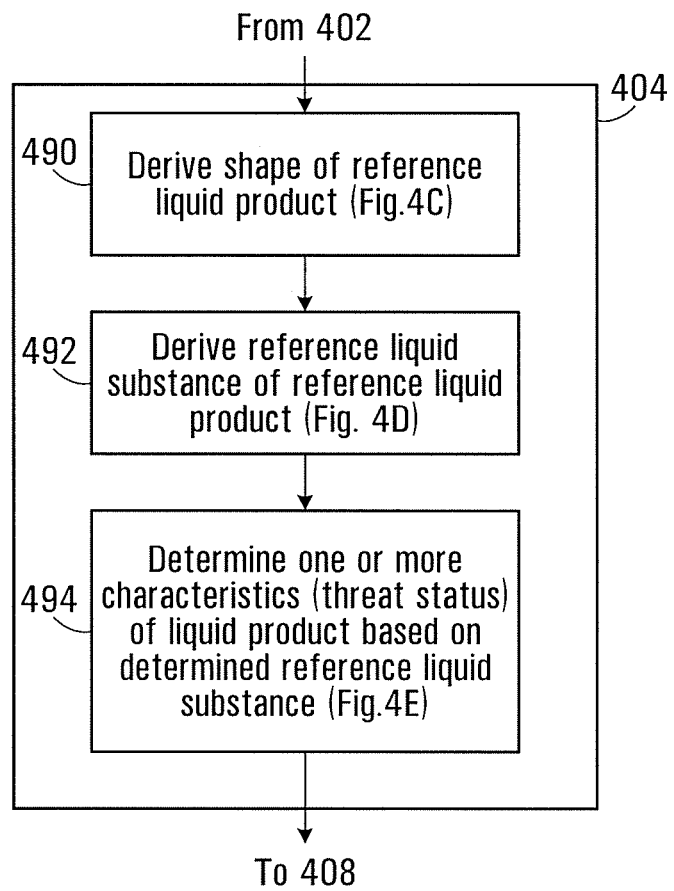

With reference to FIG. 4B, an overall process for determining one or more characteristics of a liquid product under inspection in accordance with a specific example of implementation is shown. In a practical implementation, steps 490, 492 and 494 in FIG. 4B are implemented by the various components 308, 310, 314 and 312 of the processor 302 depicted in FIG. 3.

At step 490, shape information associated with a reference liquid product is derived. In a specific example, the shape information associated with the reference liquid product is derived at least in part based on the X-ray image data associated with the liquid product under inspection (received at step 402 shown in FIG. 4A). In a non-limiting implementation, the shape information associated with the reference liquid product derived at step 490 is a mathematical representation including information conveying:

an approximate three-dimensional shape of the bottle of the liquid product under inspection;

an approximate indication of the level of the liquid in the bottle of the liquid product under inspection;

location information of the liquid product under inspection with reference to the X-ray source and the X-ray detectors in the inspection device 102.

At step 492, a reference liquid substance is derived. In a specific example, the reference liquid substance derived at step 492 potentially corresponds to the liquid substance held by the liquid product under inspection. Optionally, step 492 also generates a confidence level indicating how likely it is that the reference liquid substance corresponds to the liquid substance held by the liquid product under inspection.

At step 494, one or more characteristics of the liquid product under inspection are derived based on the reference liquid substance determined at step 492 and, optionally, the confidence level associated with the reference liquid substance.

Following step 494, the process then proceeds to step 408 described above with reference to FIG. 4A.

Figure 4C:
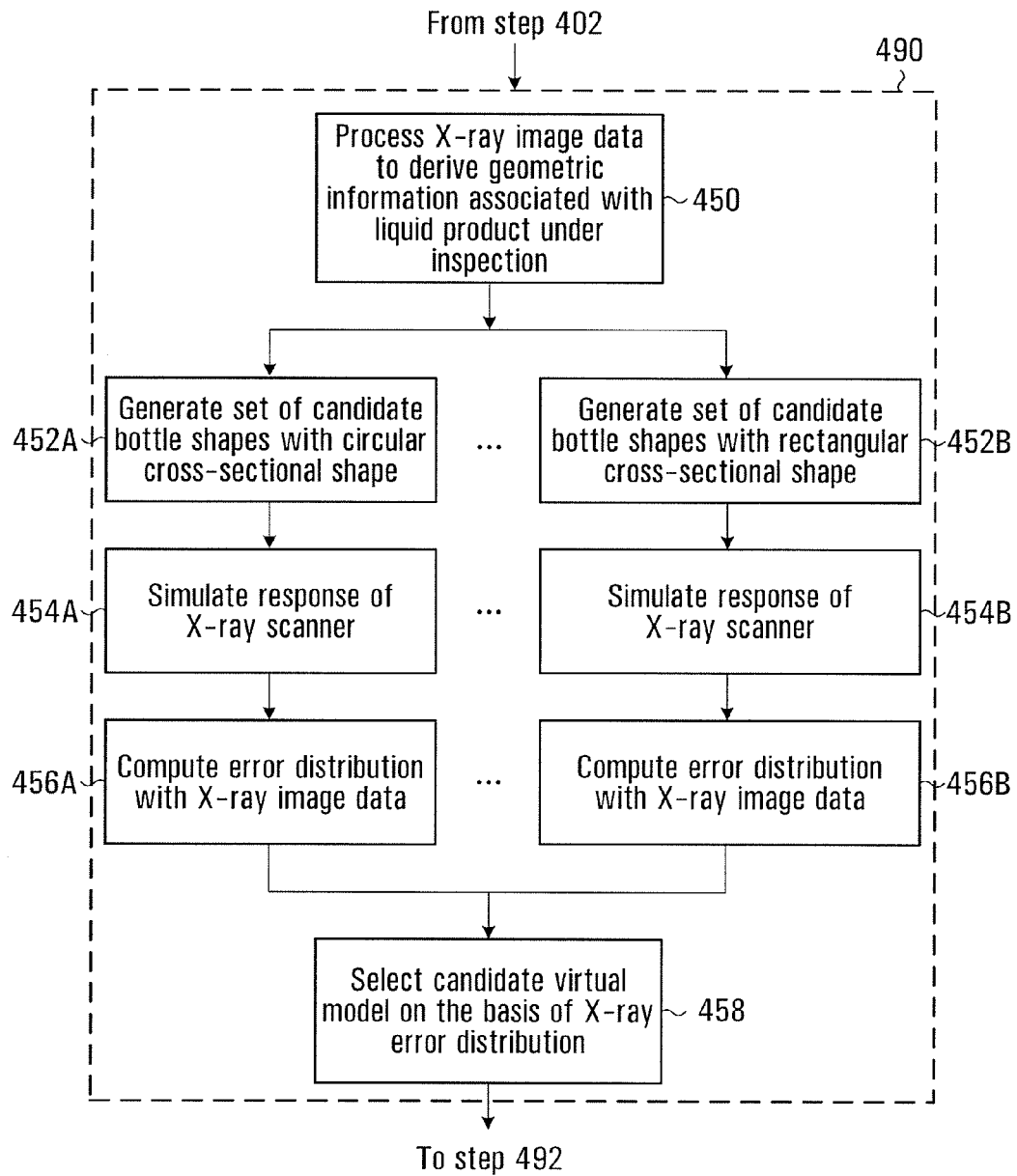

A specific example of implementation of step 490 will now be described with reference to FIG. 4C.

As shown, at step 450 the X-ray image data received from the inspection device 102 (shown in FIG. 1) is processed to derive geometric information associated with the bottle of the liquid product under inspection. The derived geometric information associated with the bottle may include one or more of the following elements:

Approximation of the bottle height;
Approximation of the bottle width;
Approximation of the bottle length;
Approximation of the profile of the bottle;
Approximation of the position of the bottle in the tray;
Location and orientation of longitudinal axis of the bottle;
In an implementation in which the liquid product is positioned on a tray having a bottom surface with a known inclination, the angle made between a longitudinal axis of the bottle and a horizontal plane is used to derive the geometric information associated with the bottle;
Location information of the liquid product under inspection with reference to the X-ray source and the X-ray detectors in the inspection device 102 (shown in FIG. 1).

In implementations in which the inspection device 102 (shown in FIG. 1) is a "multi-view" type X-ray machine generating multiple two-dimensional image of the liquid product, the multiple images may be used to obtain additional information as to the size, shape and positioning of the bottle. Several suitable methods for extracting geometric information from an image are known in the art of computer vision and as such will not be described in further detail here.

At steps 452A-B, a set of candidate bottle shapes is generated based on the geometric information derived at step 450. The candidate bottle shapes are mathematical representation of the shapes of bottles. The person skilled in the art will appreciate that, although there may be some exceptions, most bottles have shapes exhibiting symmetrical properties. For instance, several bottles exhibit some level of rotational symmetry along their longitudinal axis. In a specific non-limiting example of implementation, generating three-dimensional candidate bottle shapes is effected by:

using the location and orientation of its longitudinal axis obtained at step 450;
using the length and width of the bottle obtained at step 450;
(optionally) using the shape of the profile of the bottle along one side of the longitudinal axis obtained at step 450; and
extrapolating all other points on the bottle by effecting a rotation of the profile of the bottle around the longitudinal axis using a reference cross-sectional shape obtained at step 450.

In a specific example of implementation, the set of candidate bottle shapes have different cross-sectional shapes including, without being limited to, a generally circular shape, a generally elliptical shape, a generally rectangular shape and a generally square shape. The set of candidate bottle shapes generated at steps 452A-B are associated with location information positioning the candidate bottle shape with reference to the X-ray source and the X-ray detectors in the inspection device 102 (shown in FIG. 1).

Figure 6B:
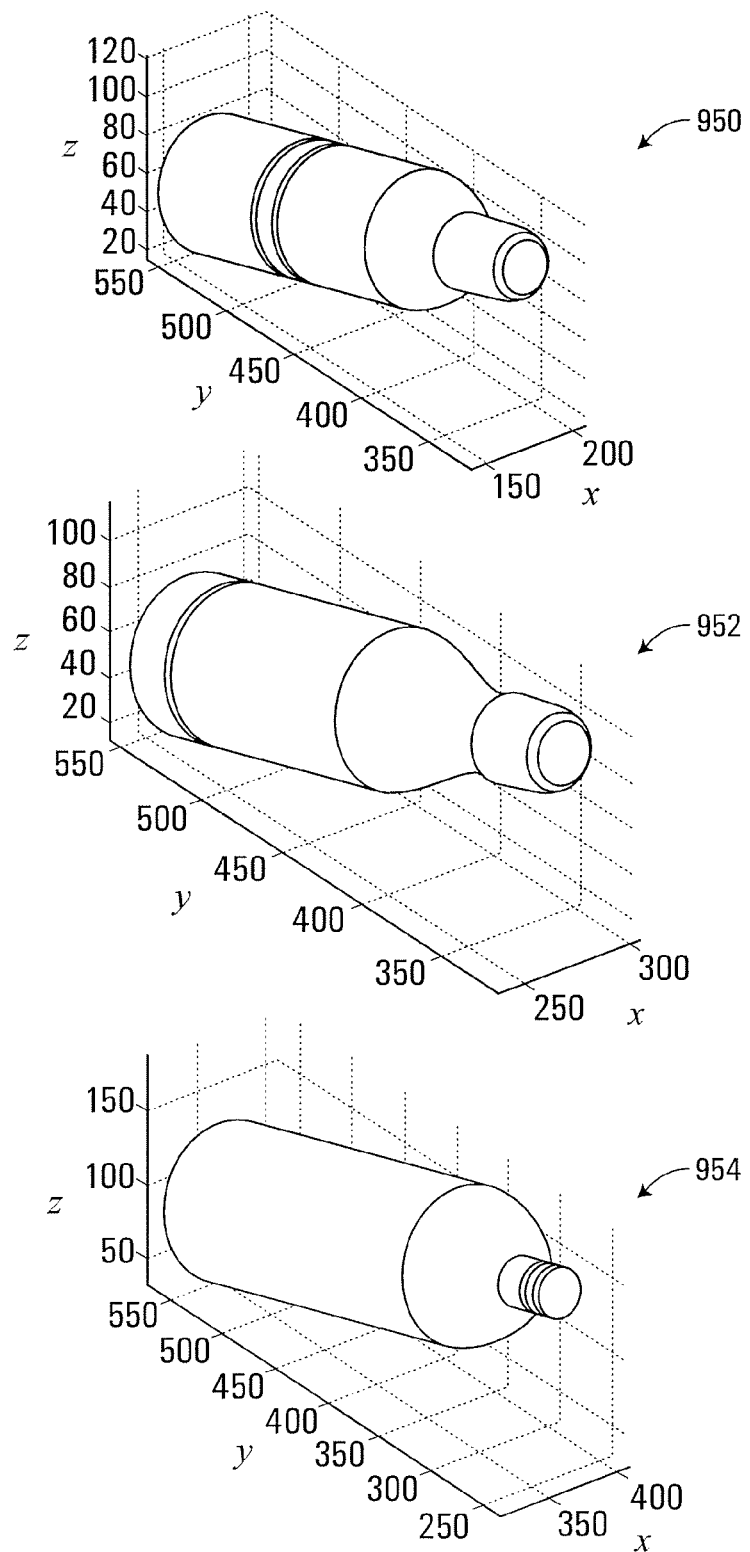
FIG. 6B shows visual representations of reconstructed 3-D images of the three (3) bottles depicted in the X-ray image of FIG. 6A in accordance with a specific example of implementation of the invention.

FIG. 6B of the drawings shows in graphical form three-dimensional mathematical representations 950, 952 and 954, which correspond respectively to the bottles 900, 902 and 904 depicted in the X-ray image shown in FIG. 6A.

At steps 454A-B, the candidate bottle shapes generated at steps 452A-B are processed to generate simulated responses to X-rays.

In a non-limiting example of implementation, each candidate bottle shape generated at steps 452A-B is processed to derive one or more virtual models, wherein each virtual model corresponds to a respective reference liquid product. In a non-limiting example of implementation, for each candidate bottle shape generated at steps 452A-B, virtual models are generated:

a) Models assuming a bottle shape corresponding to the candidate bottle shape derived in one of steps 452a-b;
b) Models assuming different types of bottle materials (e.g. glass, plastic, aluminum);
c) Models assuming different amounts of liquid in the bottle (different levels of fill); and
d) Models assuming a default liquid substance (e.g. water).

As will be appreciated by the person skilled in the art, based on the assumed level of fill of the virtual model, the length of the paths followed by X-rays through the body of liquid in the virtual model may vary. For example, for a given bottle shape, multiple levels of fill may be considered (e.g. 25% full of liquid, 50% full of liquid, 75% full of liquid, 100% full of liquid). It is to be appreciated that the number of levels of fill considered is not limiting and will depend on the desired degree of precision to be attained. It is also to be appreciated that different combinations of levels of fill (height of meniscus) and types of bottle material may be processed in parallel or sequentially depending on the processing capability of the processing module 112 (shown in FIG. 1).

In the manner described above, sets of virtual models are obtained, wherein each set of virtual models is associated with a respective candidate bottle shape. Each virtual model corresponds to a reference liquid product associated with characterization data, including:

bottle shape information derived at one of steps 452A-B;
positioning information for positioning the reference product relative to a source of X-rays derived at one of steps 452A-B;
default liquid substance information (in a non-limiting example of implementation, the default liquid substance is taken to be water although any other reference liquid substance could be used);
(optionally) a type of bottle material;
a level of fill.

In implementations in which the liquid products are supported by a tray during scanning by the inspection device 102 (shown in FIG. 1), the virtual model corresponding to the reference liquid product may further include information modeling characteristics of a reference tray corresponding to the "real" tray supporting the "real" liquid product. For the purpose of simplicity, the present description will not describe in detail the modeling of the tray since manners in which the tray may be modeled will become apparent to the person skilled in the art in light of the present description.

Following this, for each virtual model, a response of the corresponding reference liquid product to X-rays is simulated to generate simulated X-ray image data.

The purpose of the simulation is to be able to predict output intensity of the X-ray inspection device 102 (shown in FIG. 1) at high and low energy based on some level of knowledge (or assumption) of the chemical formula, density and optical path length of a reference material or object. The simulation is performed using a computer implemented simulation engine and is a coarse modelling of the operation of the X-ray inspection device 102 (shown in FIG. 1). Generally, the simulation aims to derive the likely X-ray attenuation data that would be obtained when a liquid product having shape information corresponding to that generated at one of the steps 452A-B, filled with a reference liquid, such as water for example, and having a certain level of fill (and optionally having a bottle made with a certain reference material) is screened by the X-ray inspection device 102. One example of a model that can be used is one which determines the attenuation to which the X-rays would be subjected, at different locations throughout the reference liquid product on the basis of theoretical equations that map attenuation with path length, liquid characteristics and X-ray characteristics. The type of bottle material and the default liquid substance in the bottle provide information pertaining to chemical formula and/or density of the material(s) through which X-rays would travel between the X-ray source and detectors of the X-ray inspection device 102 (shown in FIG. 1). It should be noted that:

- the X-ray characteristics of the inspection device 102 can be modelled;
- the liquid characteristics of the default liquid substance (e.g. water) are known;
- the length of the path taken by X-ray through the reference liquid product can be derived based on the virtual model; and
- an estimate of the attenuation information can be derived based on the X-ray characteristics of the inspection device 102, the liquid characteristics of the default liquid substance and the path length information.

The result of steps 454A-B is a plurality of simulated X-ray images where each simulated X-ray image conveys simulated attenuation information in the form of a two-dimensional X-ray image and is associated with a respective reference liquid product having a respective shape and holding a default liquid substance (e.g. water).

At steps 456A-B, the simulated X-ray images obtained at steps 454A-B are compared to the X-ray image data associated to the liquid product under inspection, also referred to as the "real" X-ray image data, and which was received by the processing module at step 402 (shown in FIG. 4*a*). The purpose of the comparison is to determine the difference between the two. In a non-limiting example of implementation, an error distribution map conveying differences in attenuation between the "real" X-ray image data and the simulated X-ray image data is generated for each reference liquid product. This error distribution map can be generated, for example, by subtracting the "real" X-ray image data and the simulated X-ray image data on a pixel by pixel basis. As will be appreciated by the person skilled in the art, the error distribution maps convey information pertaining to the magnitude, as well as the distribution of the differences in attenuation between the "real" X-ray image data and the simulated X-ray image data. Each error distribution map provides an indication as to how closely the characterization data of a corresponding reference liquid product approximates that of the liquid product under inspection.

It will be appreciated by the person skilled in the art that the attenuation information generated by the reference liquid product will likely be different from the attenuation information in the "real" X-ray image data since the liquid substances are likely different. Recall that the reference liquid product uses a default liquid substance (such as water), while the liquid product under inspection is most likely filled with another liquid substance. However, if the candidate shape of the bottle and currently estimated level of fill are generally correct, the attenuation error distribution will be generally uniform. On the other hand, if the currently estimated level of fill and/or candidate shape of the bottle is far from those of the liquid product under inspection, then the error distribution will not be uniform.

At step 458, the results of the comparisons performed at steps 456A-B are processed to select a virtual model from the sets of candidate virtual models, wherein the selected virtual model corresponds to a reference liquid product. As indicated above, each error distribution map provides an indication as to how closely the characterization data of an associated reference liquid product approximates that of the liquid product under inspection. During this step, the error distribution maps are processed to identify a distribution map in which the magnitude and the variations of the differences in attenuation between the "real" X-ray image data and the simulated X-ray image data are smaller than the other error distribution maps. The reference liquid product associated with the identified error distribution map is then selected.

The result of step 458 is characterization data conveying shape information associated with a reference liquid product, where the shape information approximates the shape of the liquid product under inspection.

The process then proceeds to step 492 where a reference liquid substance is derived.

Figure 4D:
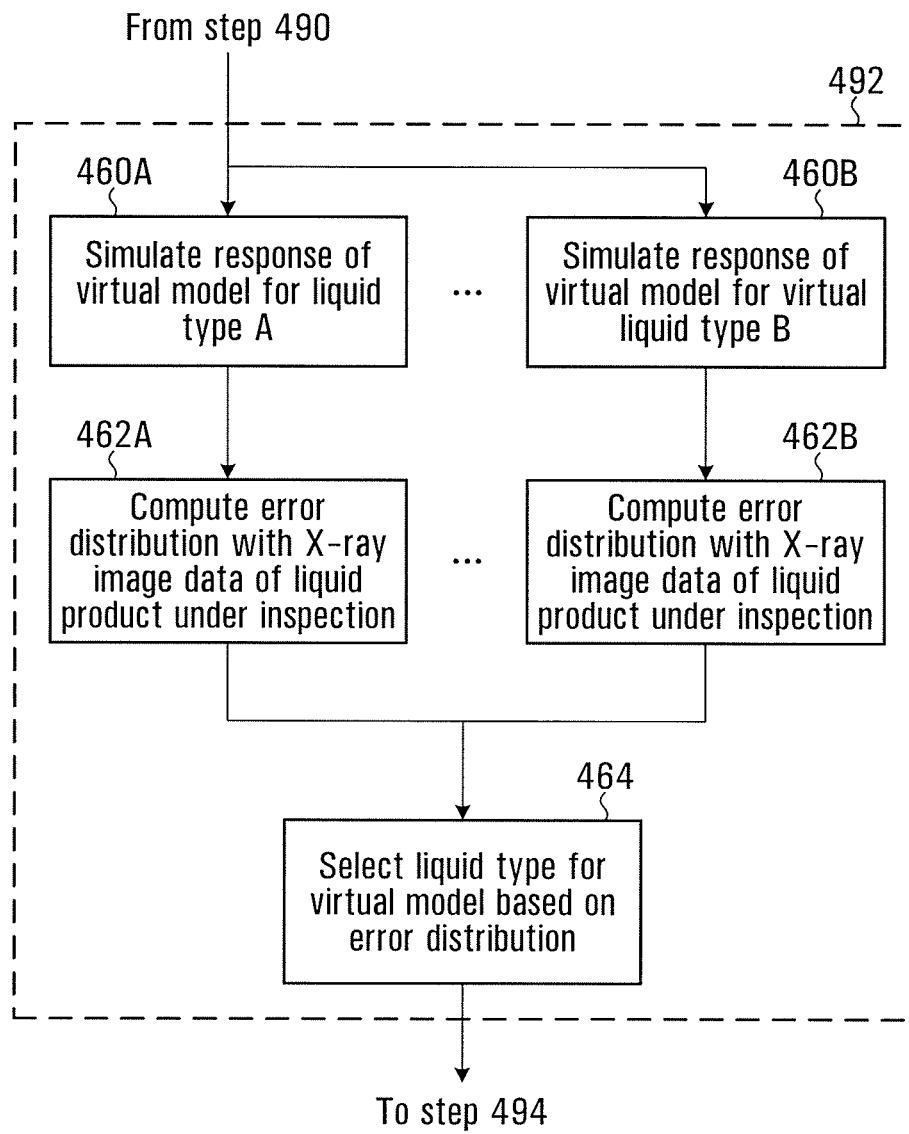

A specific example of implementation of step 492 will now be described with reference to FIG. 4D.

As depicted, at steps 460A-B the shape information associated with the reference liquid product derived at step 490 (shown in FIG. 4B) is processed to generate a set of simulated X-ray responses, where each simulated response to X-rays is associated with a different liquid substance. More specifically, at steps 460A-B a set of reference liquid products is generated, where each reference liquid product is associated with characterization data including:

- the shape information derived at step 490 (shown in FIG. 4B), including fill level;
- a respective liquid substance from a set of liquid substances.

The set of liquid substances may include any number of liquid substances and types of substances. In a specific practical implementation, the set of liquid substances includes one or more liquid substances constituting "threat" and one or more liquid substances deemed to be "safe".

Following this, for each reference liquid product, a response to X-rays is simulated to generate simulated X-ray image data. The candidate shape information derived at step 490 is used to obtain optical path length information through the body of liquid of the reference liquid product. The liquid substance for each reference product provides information pertaining to chemical formula and or density of the material(s) through which X-rays would travel between the X-ray source and detectors of the X-ray inspection device 102 (shown in FIG. 1).

The result of steps 460A-B is a plurality of simulated X-ray images where each simulated X-ray image conveys simulated attenuation information in the form of a two-dimensional X-ray image and is associated with a respective reference liquid product holding a respective liquid substance and characterized with the same shape information derived at step 490.

Following this, at steps 462 A-B, the simulated X-ray images obtained at steps 460A-B are compared to the X-ray image data associated to the liquid product under inspection, also referred to as the "real" X-ray image data, and which was received by the processing module 112 at step 402 (shown in FIG. 4A). In a non-limiting example of implementation, an error distribution map conveying differences in attenuation between the "real" X-ray image data and the simulated X-ray image data is generated for each reference liquid product.

At step 464, the results of the comparisons performed at steps 462A-B are processed to select a virtual model from the sets of candidate virtual models, wherein the selected virtual model corresponds to a reference liquid product. During this step, the error distribution maps are processed to identify a distribution map in which the magnitude as well as the variations of the differences in attenuation between the "real" X-ray image data and the simulated X-ray image data are smaller than the other error distribution maps. The reference liquid product associated with the identified error distribution map is then selected.

The result of step 464 is characterization data conveying shape and liquid content information associated with a reference liquid product, where the shape information and the liquid content information approximates the shape and liquid content of the liquid product under inspection. Optionally, step 464 also generates a confidence level indicating how likely it is that the reference liquid substance corresponds to the liquid substance held by the liquid product under inspection. The confidence level is derived at least in part based on the error distribution map associated with the selected reference product and may be derived using any suitable manner.

The process then proceeds to step 494 where one or more characteristics of the liquid product under inspection are derived based on the reference liquid substance determined at step 492.

Figure 4E:
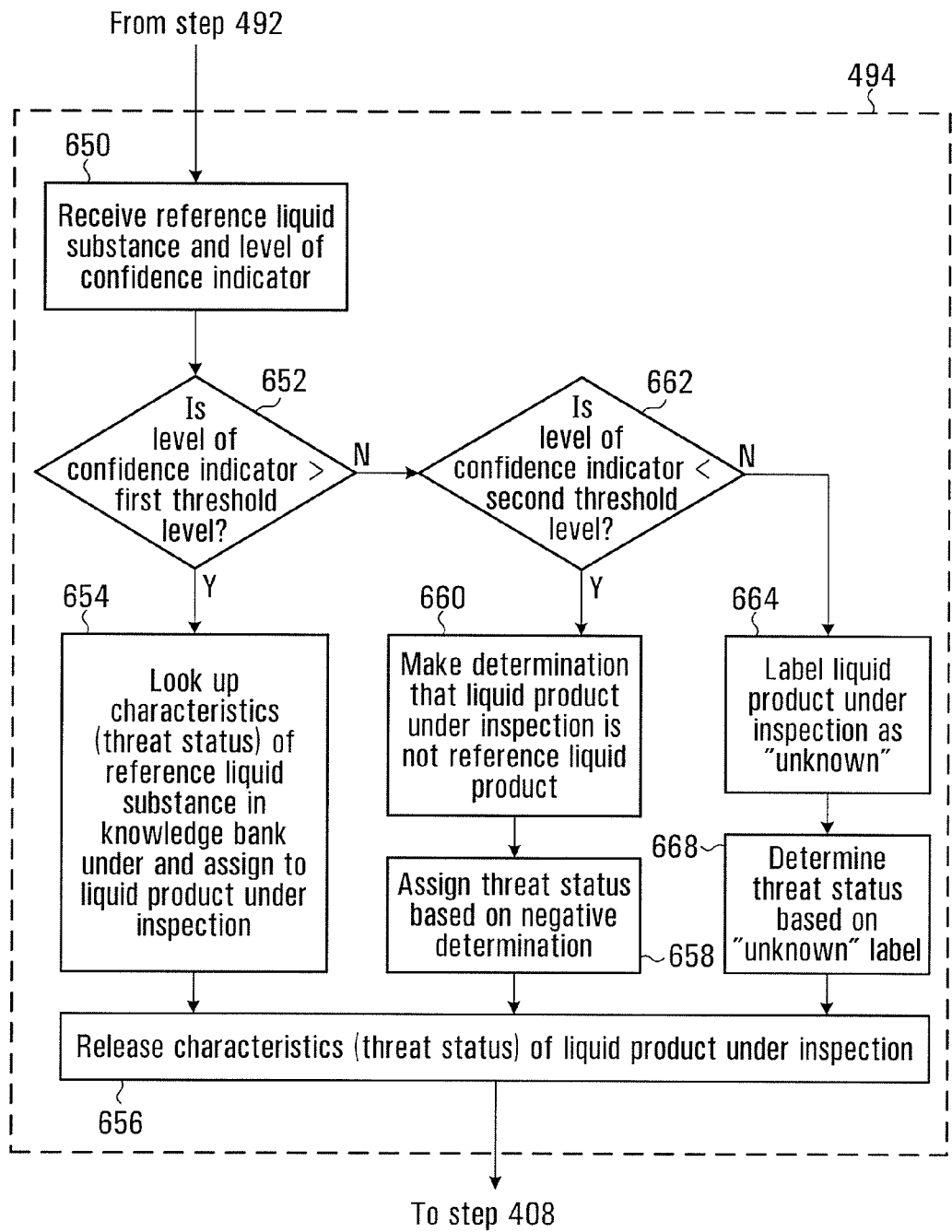

A specific example of implementation of step 494 will now be described with reference to FIG. 4E.

At step 650, the reference liquid substance and the level of confidence are received, where the level of confidence indicates how likely it is that the reference liquid substance corresponds to the liquid substance held by the liquid product under inspection.

At step 652, the level of confidence received at step 650 is compared against a first threshold level of confidence. If the level of confidence exceeds the first threshold, thereby indicating that the reference liquid substance is likely to correspond to the liquid substance held by the liquid product under inspection, the process proceeds to step 654. If the level of confidence does not exceed the first threshold, the process proceeds to step 662.

At step 654, which is initiated when the reference liquid substance is likely to correspond to the liquid substance held by the liquid product under inspection, the characteristics of the liquid product under inspection, including for example its threat status, can be inferred from the characteristics of the reference liquid substance. In particular, the reference liquid substance obtained at step 492 (shown in FIG. 4B) is associated to characteristics such as, but not limited to, a threat status, material density, material type, material chemical formula, one or more linear attenuation coefficients and/or an effective atomic number ($Z_{eff}$ number). These characteristics of the reference liquid substance may be stored on a computer readable memory module, such as the memory 306 (shown in FIG. 3). In a specific example, the characteristics of the liquid product under inspection may be determined by a simple look-up procedure by using the reference liquid substance determined at step 492 to access a corresponding entry in the memory 306. The process then proceeds to step 656, which is described below.

At step 662, which is initiated when the level of confidence received at step 650 does not exceed a first threshold level of confidence, the level of confidence received at step 650 is compared against a second threshold level of confidence that is the same or lower than the first level of confidence. If the level of confidence is lower that the second threshold, thereby indicating that the reference liquid substance is unlikely to correspond to the liquid substance held by the liquid product under inspection, the process proceeds to step 660. If the level of confidence is at least as high as the second threshold, the process proceeds to step 664.

At step 660, which is initiated when the reference liquid substance is unlikely to correspond to the liquid substance held by the liquid product under inspection, a negative determination of the liquid product under inspection is made. For example if the reference liquid substance is water and is associated with a low likelihood of corresponding to the liquid held by the liquid product under inspection, step 660 determines that the liquid held by the liquid product is unlikely to be water. The process then proceeds to step 658.

At step 658, a threat status is assigned to the liquid product under inspection based in part on the negative determination made at step 660. For example, if the reference liquid substance is associated with a "safe" threat status from a set of "safe" substances and it is determined at step 660 that the liquid held by the liquid product is unlikely to correspond to this reference liquid substance, then at step 658 a "prohibited" (or equivalent) threat status may be assigned to the liquid product under inspection irrespective of whether the content or not the liquid held by the liquid product constitutes a threat. The reverse type of logic may also be contemplated. For example, if the reference liquid substance is a "prohibited" liquid substance from a set of "prohibited" substances, and it is determined at step 660 that the liquid held by the liquid product is unlikely to be the "prohibited" substance, then at step 658 a "safe" (or equivalent) threat status may be assigned to the liquid product under inspection irrespective of whether the content or not the liquid held by the liquid product constitutes a threat. It is to be appreciated that this latter type of logic leaves open the possibility that if the liquid product under inspection holds a dangerous liquid substance that is not in the set of set of "prohibited" substances contemplated by the system, the process shown in figure will erroneously assign a "safe" (or equivalent) threat status to the liquid product. Therefore, practical implementations of this process would preferably take this consideration into account when assigning a threat status at step 658.

Once a threat status has been assigned to the liquid product under inspection at step 658, the process proceeds to step 656 described below.

Returning now to step 664, which is initiated when the level of confidence received at step 650 is between the first and the second threshold level of confidence, the liquid product under inspection is labelled as being unknown. In other words, the process was neither able to provide a sufficiently high level of confidence that the reference liquid substance either corresponded to the liquid product under inspection or a sufficiently low level to rule out the possibility that it may correspond to that reference liquid substance. The process then proceeds to step 668.

At step 668, a threat status is assigned to the liquid product under inspection based in part on the "unknown" label assigned at step 664. At this step, any suitable rule may be used to assign a threat status. In a non-limiting example of implementation, all liquid products labelled as "unknown" are assigned a "prohibited" (or equivalent) threat status. Once a threat status has been assigned to the liquid product under inspection, the process proceeds to step 656.

At step 656, the characteristics of the liquid product under inspection determined at one of steps 654, 658 and 668, are released and the process proceeds to step 408 described above with reference to FIG. 4A.

X-Ray Simulator

As described above, the processing module 112 includes an X-ray simulator device 310 (shown in FIG. 3) which implements a process for simulating responses of reference products to X-rays. The purpose of the simulation is to be able to predict output intensity of the X-ray inspection device 102 (shown in FIG. 1) at high and low energy based on some level of knowledge (or assumption) of the chemical formula, density and optical path length of a reference material or product that would be positioned in the X-ray path.

A specific example of implementation of the X-ray simulator device 310 (shown in FIG. 3) will be described below with reference to FIG. 7 of the drawings. It is to be appreciated that this description is being presented for the purpose of illustration only and that many other suitable devices for simulating X-ray responses may be contemplated in the art in light of the present description.

Figure 7:
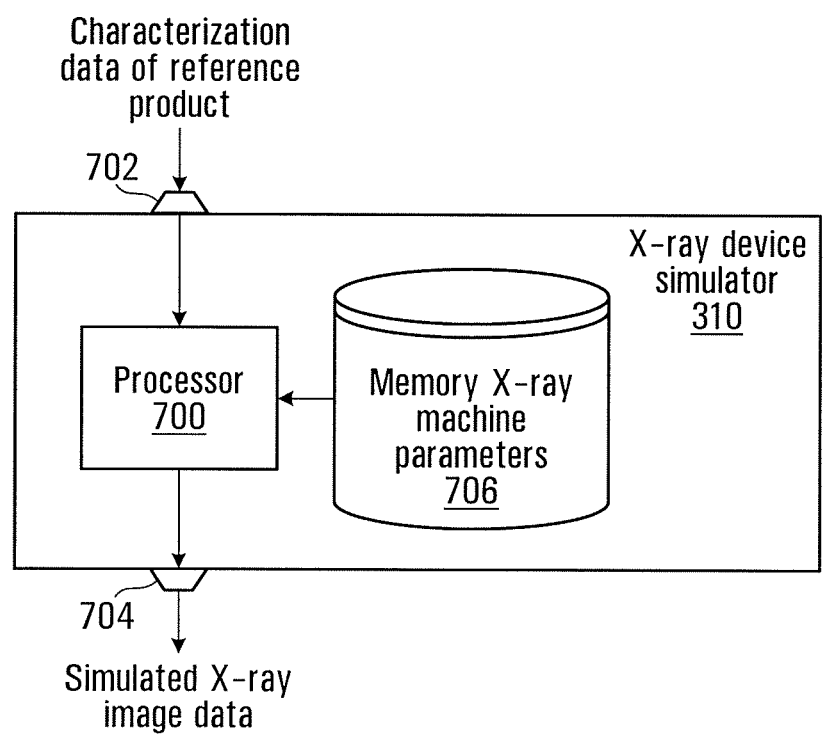
FIG. 7 is a block diagram of an X-ray simulator device suitable for use in connection with the processing module depicted in FIG. 3 in accordance with a specific example of implementation of the invention.

As depicted in FIG. 7, the X-ray simulator device 310 includes an input 702 for receiving characterization data associated with a reference product, a processor 700 for processing the characterization data and generate simulated X-ray image data and an output 704 for releasing the simulated X-ray image data generated by the processor 700. In the specific example depicted, the X-ray simulator device 310 also includes a memory module 706 storing a plurality of parameters related to the inspection device (such as for example, the inspection device 102 shown in FIG. 1) whose behaviour the X-ray simulator 310 is configured to simulate.

In a specific implementation, the input 702 receives characterization data associated with a reference product from the reference product generator 308 (shown in FIG. 3). The characterization data received provides information pertaining to material properties and physical dimensions of the reference product from which optical path length and material properties (linear attenuation coefficient, effective atomic number ($Z_{eff}$), material density, and/or chemical formula) can be derived. In cases where the reference product is a reference liquid product, the characterization data may include, for example:

bottle shape information;
positioning information for positioning the reference liquid product relative to a source of X-rays;
liquid substance information;
(optionally) type of bottle material;
a level of fill.

The processor 700 is configured to process the characterization data received at input 702 to generate simulated X-ray image data associated with the reference product by modelling interactions between X-rays and the reference product. In a specific example of implementation, the processor 700 determines the degrees to which an X-ray is attenuated between an X-ray source and a detector as it passes through the reference product. Generally speaking, the degree to which an X-ray is attenuated between an X-ray source and a detector is a function of the properties of the substances/materials it passes through, as well as the lengths of the paths travelled by the X-ray through each one of the substances/materials.

In a specific example of implementation, the processor 700 processes the characterization data received at input 702 to derive optical path length and material properties (linear attenuation coefficient, effective atomic number ($Z_{eff}$), material density, and/or chemical formula) of the paths taken by X-rays between the source of X-rays and detectors. Based on this derived information, the processor 700 determines the attenuation to which the X-rays would be subjected, at different locations throughout the reference liquid product on the basis of theoretical equations that map attenuation with path length, liquid characteristics and X-ray characteristics.

Figure 8:
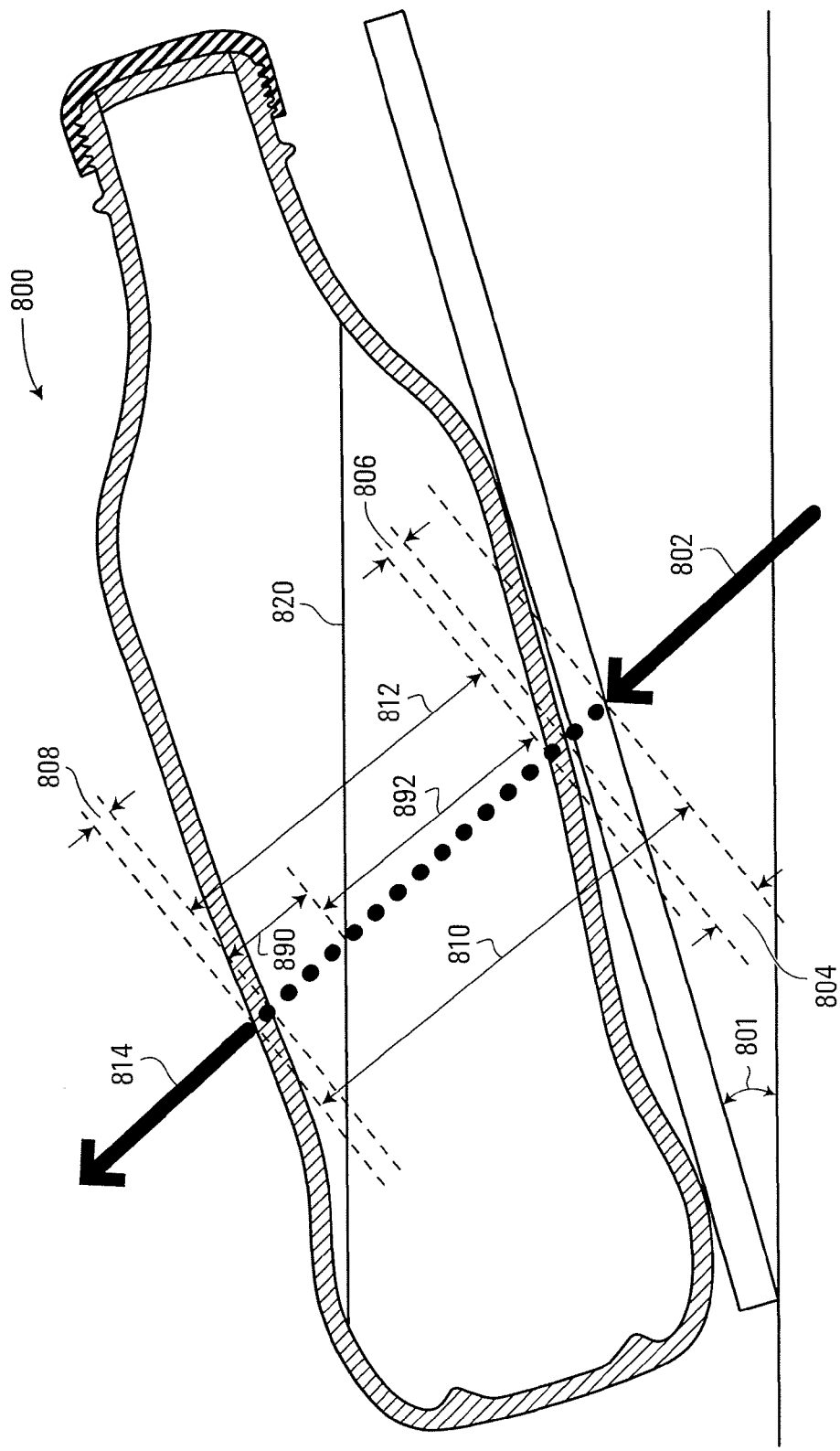
FIG. 8 is a cutaway side view of a bottle partially filled with liquid and maintained in an inclined position in accordance with a non-limiting example of implementation of the invention.

FIG. 8 illustrated in graphical form a side cutaway view of a reference liquid product 800 that may be conveyed by characterization data. As shown, the reference liquid product 800 is generally inclined at an angle 801 relative to a generally horizontal plane and is supported by a tray which is also modelled by characterization data. FIG. 8 also shows a path taken by a ray of penetrating radiation (i.e. an X-ray) through the reference liquid product 800. The X-ray enters the reference liquid product 800 at location 802, travels through the bottle walls and the bottle contents, and emerges from the bottle at location 814. The angle between the X-ray and the longitudinal axis of the bottle of liquid can be derived using simple trigonometry since the angle 801 is known and the orientation of the X-ray is also known.

As can be seen, as the X-ray travels from the X-ray source (not shown) to the X-ray detectors (not shown), the X-ray is attenuated by not only the liquid in the bottle but by a supporting structure (such as a tray and/or conveyor belt) holding the bottle, as well as the side walls of the bottle. Segment 810 between the locations 802 and 814, herein referred to as the combined segment 810, is a combination of the following segments:

segment 804 through the supporting structure (for example a tray);
segments 806 and 808 through the side walls of the bottle; and
segment 812 through the inside portion of the bottle 800.

As can be observed in FIG. 8, the position of the meniscus 820 (level of fill) is such that the length of the path segment 812, which is the length of the path through the inside portion of the bottle 800, includes a first component 892 corresponding to the length of the path taken by the X-ray passing through the liquid within the bottle but also includes a second component 890 corresponding to the length of a path taken by the X-ray in a layer of air above the meniscus.

Considering the reference liquid product depicted in FIG. 8, the processor 700 shown in FIG. 7 would make use of the characterization data to derive the path length associated with:

segment 804 through the supporting structure;
segments 806 and 808 through the side walls of the bottle;
segment 892 through the liquid within the bottle;
segment 890 through the layer of air above the meniscus.

In addition, the processor 700 shown in FIG. 7, would make use of the characterization data received at the input 702 to derive material properties (linear attenuation coefficient, effective atomic number ($Z_{eff}$), material density, and/or chemical formula) for each of the above noted paths and would determine the attenuation to which the X-rays would be subjected on the basis of theoretical equations that map attenuation with path length, liquid characteristics and X-ray characteristics.

It is to be appreciated that the X-ray characteristics and the attenuation to which the X-rays are subjected will vary from one X-ray machine model to another and may even vary between different X-ray machines of a same model. As such, in order for the X-ray simulator device 310 to simulate a particular X-ray machine model unit, calibration information must be obtained for that particular X-ray machine model unit. Obtaining this calibration information begins with an estimate of the X-ray source spectrum of the X-ray machine model unit and an estimated scintillator (detector) spectral response for different types of materials. Optionally, in order to take into account the variations in behaviour between X-ray machines of a same machine model, additional calibration information may be obtained by using tools in the form of material references at regular intervals during the use of the X-ray machine. Such material references may be positioned so as to be scanned by the X-ray beam concurrently with the scanning of a product under inspection and/or periodically in between X-ray scans.

In a specific implementation, the simulation process implemented by the X-ray simulator device 310 predicts X-ray inspection machine output intensity at high and low energies when an object having a given chemical formula (effective atomic number), density and optical path length is positioned between the source of the X-ray and the detector. The non-limiting example of implementation described below simulates the polychromatic behaviour of a pseudo dual-energy polychromatic X-ray source and corresponding polychromatic X-ray detectors. It is to be appreciated that other approaches may be used without detracting from the spirit of the invention.

For example, alternative examples of implementation, which will not be described in detail but which will become apparent to the person skilled in the art, may approximate the source of X-rays as being monochromatic and may rely on the average of the detected high spectrum and detected low spectrum for the response of the X-ray detectors. Since real physical X-ray sources have generally polychromatic distributions, it is to be appreciated that results obtained using a monochromatic approximation of the X-ray source may be less precise than those relying on a polychromatic approximation.

Nevertheless, the precision obtained using such monochromatic approximation may be sufficient in certain specific implementations.

Returning now to the specific example of implementation simulating the polychromatic behaviour an X-ray source in an X-ray inspection machine, in order to predict the X-ray inspection machine output intensity at high and low energies, the process simulates the following steps:

1. X-ray photons discrete source emission: $S_{in}(E)$ where E is in keV.
2. The attenuation of the X-ray spectrum when passing through one or plural materials of known chemical composition $$\frac{\mu_c}{\rho}(Z_{\mathit{eff}}, E),$$

density ($\rho$) and optical path length (t) where $$\frac{\mu_c}{\rho}(Z_{\mathit{eff}}, E)$$

is the compound mass attenuation coefficient computed using traceable standard mass attenuation coefficients (NIST) for each energy. Mathematically this can be expressed as follows:

$$\frac{\mu_c}{\rho}(Z_{\mathit{eff}}, E) = \sum_i \left(\frac{\mu}{\rho}(Z_i, E)\right)_i w_i \qquad \text{Equation \#1}$$

Where $w_i$ is the fraction by weight of the $i^{th}$ atomic constituent and $$\left(\frac{\mu}{\rho}(Z_i, E)\right)_i$$

are the mass attenuation coefficients at each discrete energy of the spectrum of the $i^{th}$ atomic constituent. Each atomic constituent is available in the given chemical formula of the given material/compound.

The mass attenuation coefficient is related to the chemical formula of the material. In order to represent this dependency, the mass attenuation coefficient relies on Zeff, where Zeff is computed from the chemical formula of the material using:

$$Z_{\mathit{eff}} = \sqrt[p]{\sum_i a_i \cdot Z_i^p}$$

where $a_i$ is the fractional element of electrons per gram and $Z_i$ is the atomic number of the $i^{th}$ atomic element of the chemical formula of the compound.

The attenuation of the X-ray spectrum $S_{out}(E)$, after propagation through the material of optical path length t, can then be expressed as follows:

$$S_{out}(E) = S_{in}(E) \cdot e^{-\frac{\mu_c}{\rho}(Z_{\mathit{eff}}, E) \cdot \rho \cdot t} \qquad \text{Equation \#2}$$

3. The amount of attenuation of the transmitted spectrum absorbed by the low energy scintillator (detector) of a given estimated thickness ($t_{low}$) and known mass attenuation coefficient $$\frac{\mu_s}{\rho}(Z_{\mathit{eff}}, E),$$

and density $\rho_s$ can be expressed as shown in Equations #3a and #3b below:

$$S_{low}(E) = S_{out}(E) \cdot \left[1 - e^{-\frac{\mu_s}{\rho}(Z_{\mathit{eff}}, E) \cdot \rho_s \cdot t_{low}}\right] \qquad \text{Equation \#3a}$$

$$S_{Detect\_low} = S_{in}(E) \cdot \left[1 - e^{-\frac{\mu_s}{\rho}(Z_{\mathit{eff}}, E) \cdot \rho_s \cdot t_{low}}\right] \qquad \text{Equation \#3b}$$

Where $S_{low}$ is the spectrum when it has been modified when passing through a substance and $S_{Detec\_low}$ is the spectrum when there is no object in the scene.

4. Visible photon emission (scintillation) of the low energy scintillator described by the spectral visible photon response [$\gamma_{low}(E)$] and integration by the photodiode can then be simulated. The integration of the attenuated low detected spectrum can then be normalized by the integration of itself giving us the simulated normalized grey level [0 1] of the machine:

$$I_{low} = \frac{\int_0^{E_{peak}} S_{low}(E) \gamma_{low}(E) dE}{\int_0^{E_{peak}} S_{Detect\_low}(E) \gamma_{low}(E) dE} \qquad \text{Equation \#4}$$

-continued $$= \frac{\int_0^{E_{peak}} S_{in}(E) \cdot e^{-\frac{\mu_s}{\rho}(Z_{eff},E)\rho \cdot t} \cdot \left[1 - e^{-\frac{\mu_s}{\rho}(Z_{eff},E)\rho_s \cdot t_{low}}\right] \gamma_{low}(E) dE}{\int_0^{E_{peak}} S_{Detect\_low}(E) \gamma_{low}(E) dE}$$

$$= I_{low}$$

$$= \frac{\int_0^{E_{peak}} S_{Detect\_low}(E) \cdot e^{-\frac{\mu_c}{\rho}(Z_{eff},E)\rho \cdot t} \gamma_{low}(E) dE}{\int_0^{E_{peak}} S_{Detect\_low}(E) \gamma_{low}(E) dE}$$

5. Assuming the X-ray machine being modelled is a dual energy X-ray machine, the transmission of X-rays is simulated through a copper filter medium (or other high Z material) of thickness ($t_f$) that manufacturers use to separate the high part from the low part of the spectrum. Mathematically this can be expressed as follows:

$$S_{filtered}(E) = S_{out}(E) \cdot e^{-\frac{\mu_s}{\rho}(Z_{eff},E)\rho_s \cdot t_{low}} \cdot e^{-\frac{\mu_f}{\rho}(Z_{eff},E)\rho_f \cdot t_f} \quad \text{Equation \#5}$$

$$S_{Detect\_filtered} = S_{in}(E) \cdot \left[1 - e^{-\frac{\mu_s}{\rho}(Z_{eff},E)\rho_s \cdot t_{low}}\right] \cdot e^{-\frac{\mu_f}{\rho}(Z_{eff},E)\rho_f \cdot t_f}$$

Where $S_{filtered}$ is the high energy spectrum when it has been modified when passing through a substance and $S_{Detec\_filtered}$ is the spectrum when there is no object in the scene.

6. In a specific example of implementation, an approximation is made that the majority of the filtered spectrum is absorbed by the high energy scintillator so that:

$$S_{high}(E) = S_{filtered}(E)$$

$$S_{Detect\_high}(E) = S_{Detect\_filtered}(E) \quad \text{Equation \#6}$$

7. Then step 4 above is repeated, but this time for the high energy component of the spectrum.

$$I_{high} = \frac{\int_0^{E_{max}} S_{high}(E) \gamma_{high}(E) dE}{\int_0^{E_{max}} S_{in}(E) \cdot e^{-\frac{\mu_s}{\rho}(Z_{eff},E)\rho_s \cdot t_{low}} \cdot e^{-\frac{\mu_f}{\rho}(Z_{eff},E)\rho_f \cdot t_f} \cdot \gamma_{high}(E) dE} \quad \text{Equation \#7}$$

$$= \frac{\int_0^{E_{peak}} S_{Detect\_high}(E) \cdot e^{-\frac{\mu_c}{\rho}(Z_{eff},E)\rho \cdot t} \cdot \gamma_{high}(E) dE}{\int_0^{E_{peak}} S_{Detect\_high}(E) \cdot \gamma_{high}(E) dE}$$

As will be observed, the following data for a given X-ray vendor model machine needs to be obtained or derived:

$$t_{low} \rightarrow S_{low}(E) \rightarrow \gamma_{low}(E), t_f \rightarrow S_{high}(E) \rightarrow \gamma_{high}(E)$$

In a non-limiting example of implementation, the above parameters are derived using transmission measurements of plural materials of different effective atomic numbers ($Z_{eff}$), density and thickness and primary estimation of source spectrum and scintillator spectral response coupled with a non-linear optimization algorithm.

Figure 9:
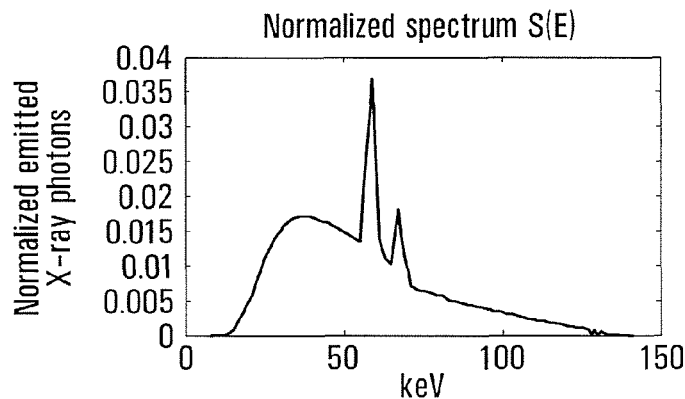
FIG. 9 is a graph depicting a source spectrum of an X-ray tungsten source in an X-ray device in accordance with a non-limiting example of implementation of the invention.

FIG. 9 is a graph depicting the source spectrum $S_{in}(E)$ for an X-ray tungsten source, which is a common X-ray source used in X-ray devices. The spectral distribution of X-ray tungsten sources is well known in the art of X-ray machines.

Figure 10:
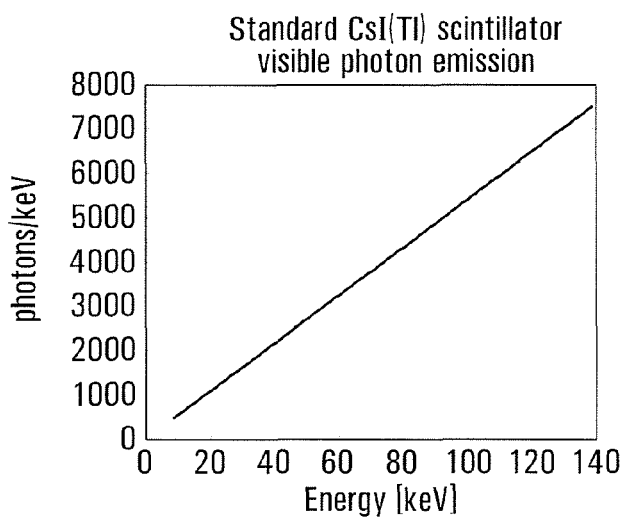
FIG. 10 is a graph depicting a theoretical scintillator response $\gamma_{low}(E)$.

The visible photon response $\gamma_{low}(E)$ can be approximated as a linear function. More specifically, in X-ray applications, the scintillator response typically produces more visible photon as the absorbed X-ray photon energy increases. FIG. 10 is a graph depicting a theoretical scintillator response [$\gamma_{low}(E)$ and $\gamma_{high}(E)$] for a typical Cesium iodide doped with thallium (CsI(Tl)) scintillator as a function of absorbed energy.

The attenuation of the X-ray spectrum can then be derived since the attenuation coefficient of the scintillator (CsI) is known from its compound formula and density and the attenuation of the copper filter is also known. Mathematically, the attenuation of the X-ray spectrum can be expressed as follows:

$$\frac{\mu_s}{\rho}(E) = \frac{\mu_{Cs}}{\rho} w_{Cs} + \frac{\mu_I}{\rho} w_I \quad \text{Using Equation \#1 above}$$

Figure 11:
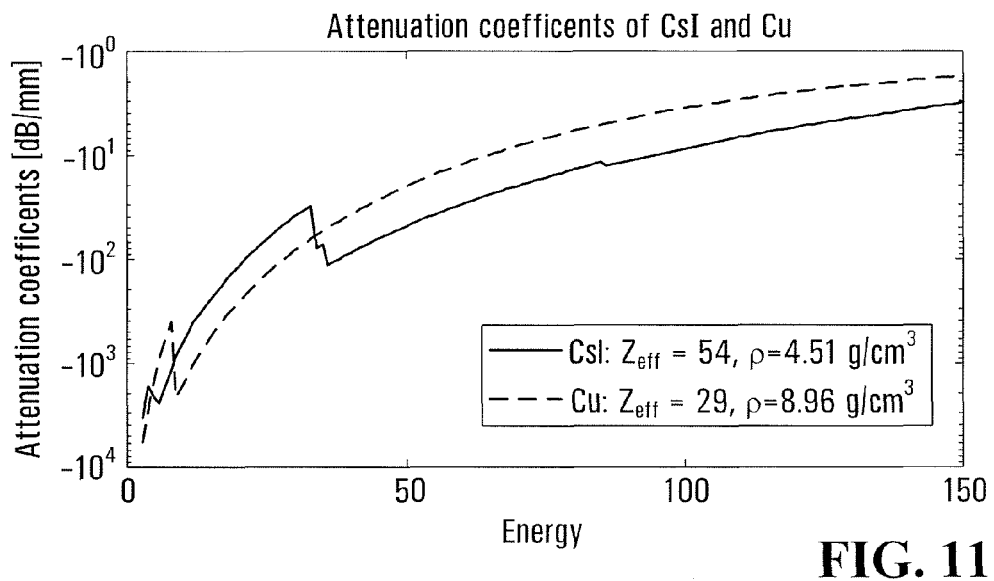
FIG. 11 is a graph showing attenuation coefficients of Cesium iodide (CsI) and copper (Cu) for different energy levels.

FIG. 11 is a graph showing the attenuation coefficients of Cesium iodide (CsI) and copper (Cu) for different energy levels. From this graph, the person skilled in the art will note the presence of "K-edges" at 33 keV for iodine and at 36 keV for the cesium.

Based on the above information, transmission/attenuation data can be obtained using known chemical formula and density materials.

Figure 12:
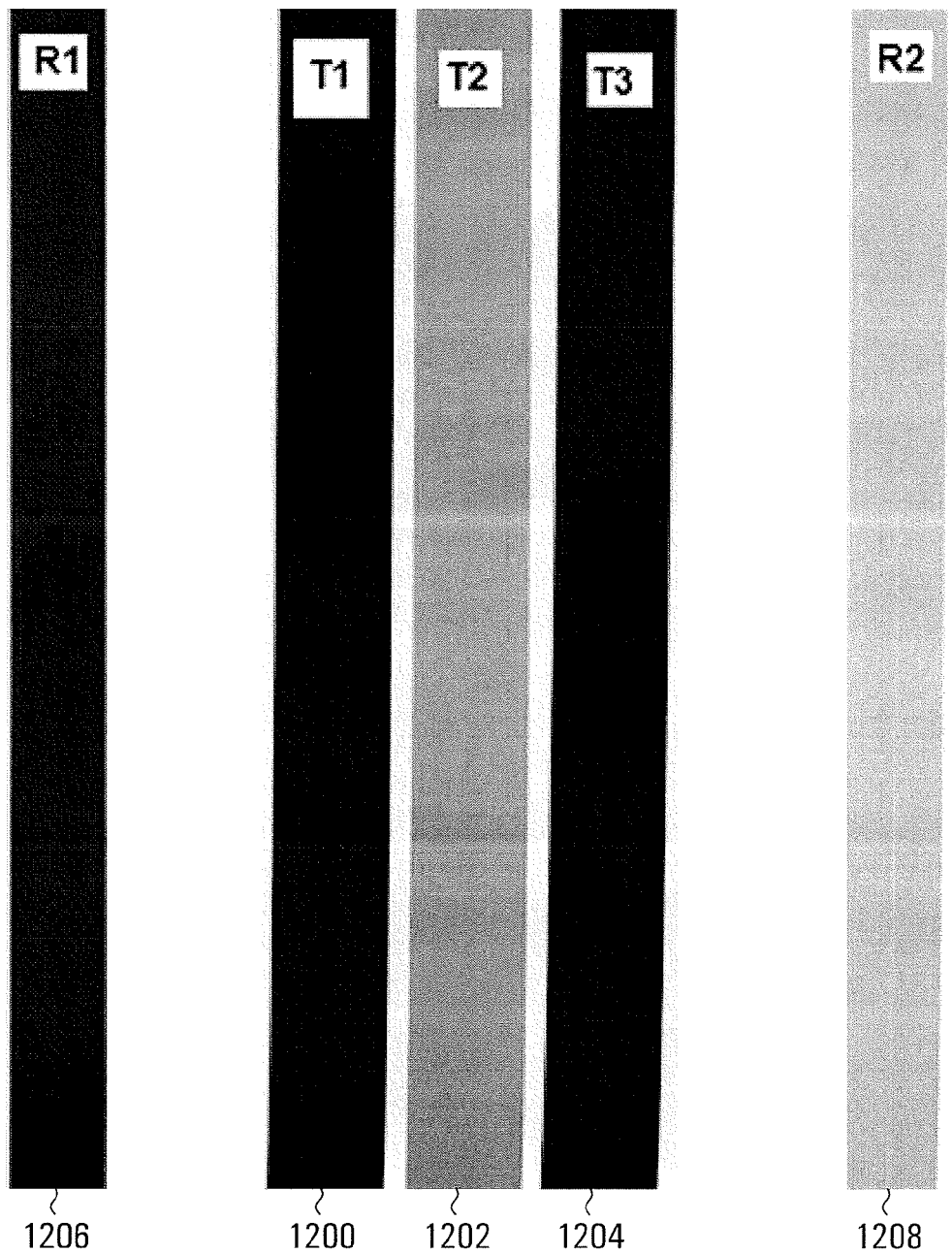
FIG. 12 shows an X-ray image derived by subjecting three (3) slabs of different materials to X-rays.

In a specific example of implementation, reference material corresponding to the limit of the detected dynamic range may further be used in order to calibrate the simulation results. FIG. 12 shows an X-ray image derived by subjecting three (3) slabs of different materials to X-rays generated by an X-ray machine whose behaviour is to be modelled. As shown, portions 1200, 1202 and 1204 correspond to the three (3) slabs of different materials and portions 1206 and 1208 correspond to additional references.

The X-ray simulator calibration steps may include the following:

A. Low detector thickness optimization:

The detected or absorbed spectrum will vary depending of the physical thickness of the scintillator (detector). In order to improve the precision of the simulation data, the value of the thickness of the scintillator used in the above model can be adjusted to better reflect the actual physical thickness of the scintillator (detector). In a specific example of implementation, using the information pertaining to the source spectrum and the approximately linear theoretical scintillator response $\gamma_{low}(E)$ shown in FIG. 10, steps 1 to 4 above are repeated for different estimated thicknesses of the low energy scintillator (detector). The relative error between M simulated low intensities and M observed low intensities is then computed using X-ray image of the slabs of material shown in FIG. 12. Following this, a low energy scintillator thickness is selected such that the error between observed low intensities on the slabs and simulated intensities values will be minimized. The estimated scintillator thickness is then used in the computation of $S_{Detect\_low}(E)$ (see equation #3b above).

Mathematically, the error may be expressed as follows:

$$\varepsilon = \frac{1}{M} \sum_{i=1}^{M} \frac{|I_{Sim\_low}(i) - I_{low}(i)|}{I_{Sim\_low}(i)} \quad \text{Equation \#8}$$

Figure 13:
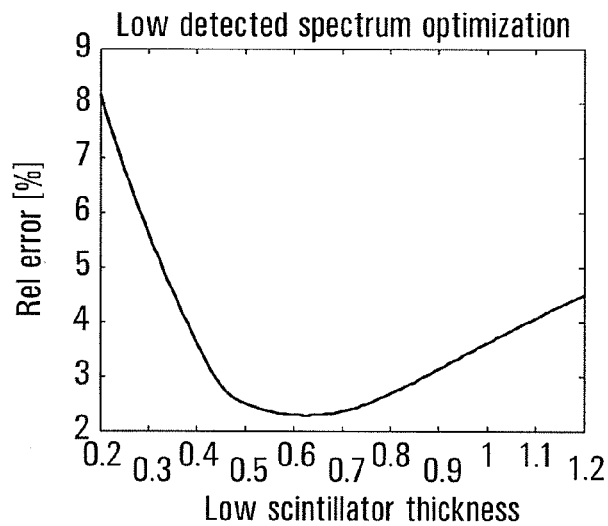
FIG. 13 is a graph showing relative errors between simulated intensities (grey levels) and the observed intensities as a function of an estimated low energy scintillator (detector) thickness, the simulated intensities being generated in accordance with a non-limiting example of implementation of the invention.

FIG. 13 of the drawings is a graph showing relative errors between the observed intensities and the simulated intensities as a function of an estimated low energy scintillator (detector) thickness based on the theoretical scintillator response $\gamma_{low}(E)$ depicted in FIG. 10.

Figure 14:
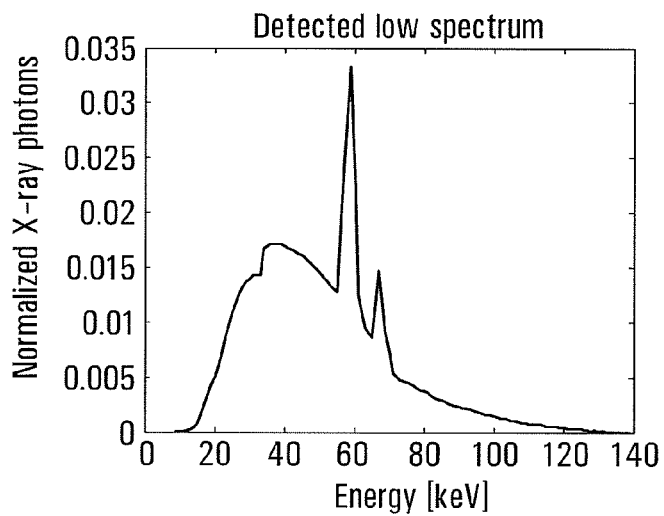
FIG. 14 is a graph depicting the detected low energy spectrum after optimisation of the low scintillator thickness.

FIG. 14 is a graph depicting the detected low energy spectrum after optimisation of the low scintillator thickness.

B. Now that we have $S_{Detect\_low}(E)$, we can use equation #4 to modify the linear approximation of $\gamma_{low}(E)$ using an error minimization algorithm.

Figure 15:
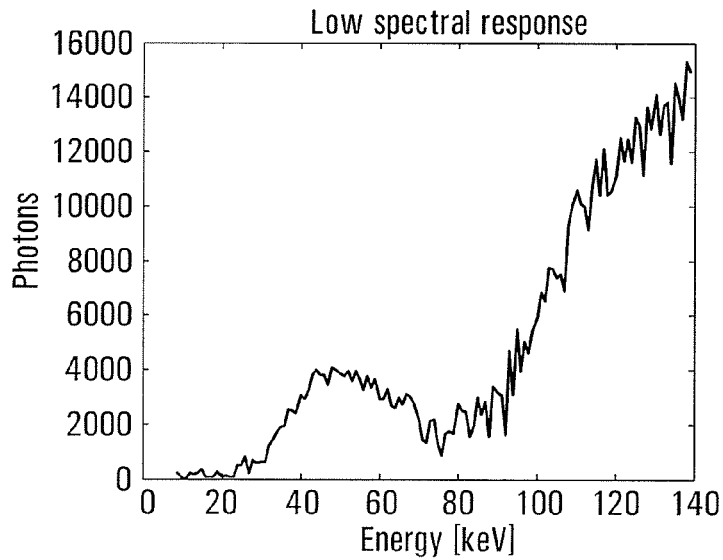
FIG. 15 is a graph depicting a spectral response obtained for the low energy scintillator optimized for a determined low scintillator thickness.

FIG. 15 is a graph showing a version the theoretical response of the scintillator $\gamma_{low}(E)$ shown in FIG. 10 optimized for a determined low scintillator thickness.

C. The above process is repeated for the high energy scintillators (detectors), repeating for different estimated thicknesses of the copper filter ($t_f$).

Figure 16:
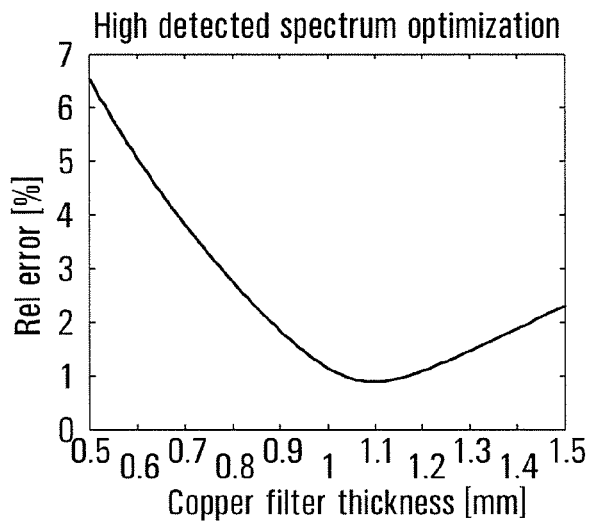
FIG. 16 is a graph showing relative errors between simulated intensities (grey levels) and the observed intensities as a function of an estimated copper filter thickness, the simulated intensities, being generated in accordance with a non-limiting example of implementation of the invention.

FIG. 16 of the drawings is a graph showing a relative error between the observed intensities and the simulated intensities as a function of an estimated copper filter thickness.

Figure 17:
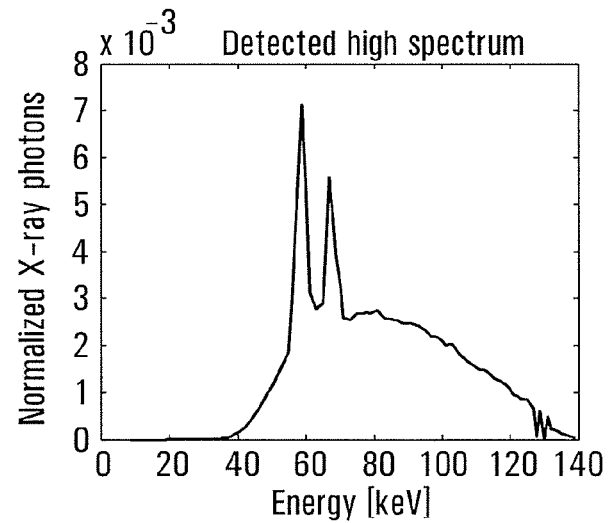
FIG. 17 is a graph depicting the detected high spectrum after copper filter thickness optimisation.

FIG. 17 is a graph depicting the detected high spectrum after copper filter thickness optimisation.

Figure 18:
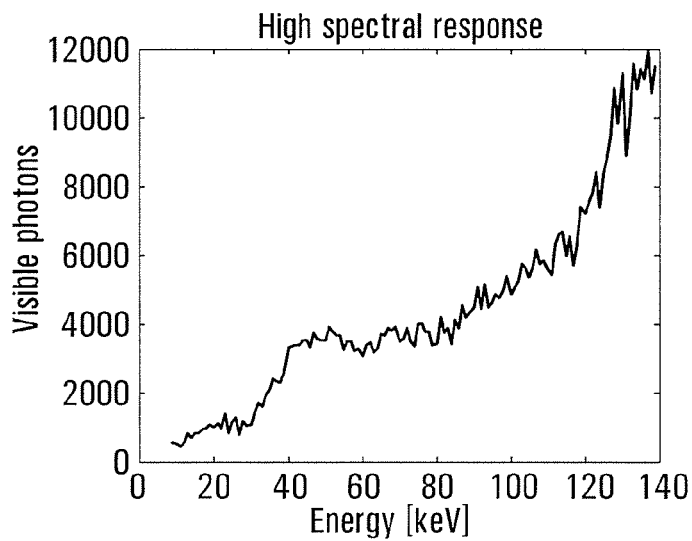
FIG. 18 is a graph depicting the high spectral response obtained for the high energy scintillator optimized for a determined copper filter thickness.

FIG. 18 is a graph showing a version the theoretical response of the scintillator $\gamma_{high}(E)$ shown in FIG. 10 optimized for a determined copper filter thickness.

Specific Practical Implementation

Figure 19:
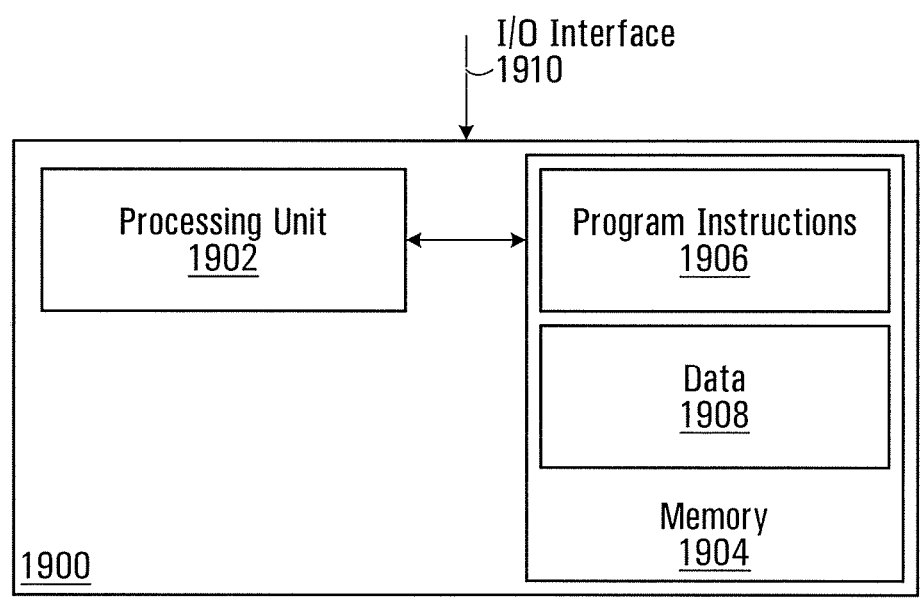
FIG. 19 is a block diagram of a computing apparatus suitable for use in connection with the processing module illustrated in FIG. 3 in accordance with a specific example of implementation of the invention.

Certain portions of the processing module 112 (shown in FIGS. 1 and 3) may be implemented on a general purpose digital computer 1900, of the type depicted in FIG. 19, including a processing unit 1902 and a memory 1904 connected by a communication bus. The memory 1904 stores data 1908 and program instructions 1906. The processing unit 1902 is adapted to process the data 1908 and the program instructions 1906 in order to implement the functions described in the specification and depicted in the drawings. The digital computer 1900 may also comprise an I/O interface 1910 for receiving or sending data elements to external devices, such as the for example the inspection device 102 and the display device 150 (both shown in FIG. 1).

Alternatively, the above-described processing module 112 can be implemented on a dedicated hardware platform where electrical/optical components implement the functions described in the specification and depicted in the drawings. Specific implementations may be realized using ICs, ASICs, DSPs, FPGA and/or other suitable hardware platform.

Figure 20:
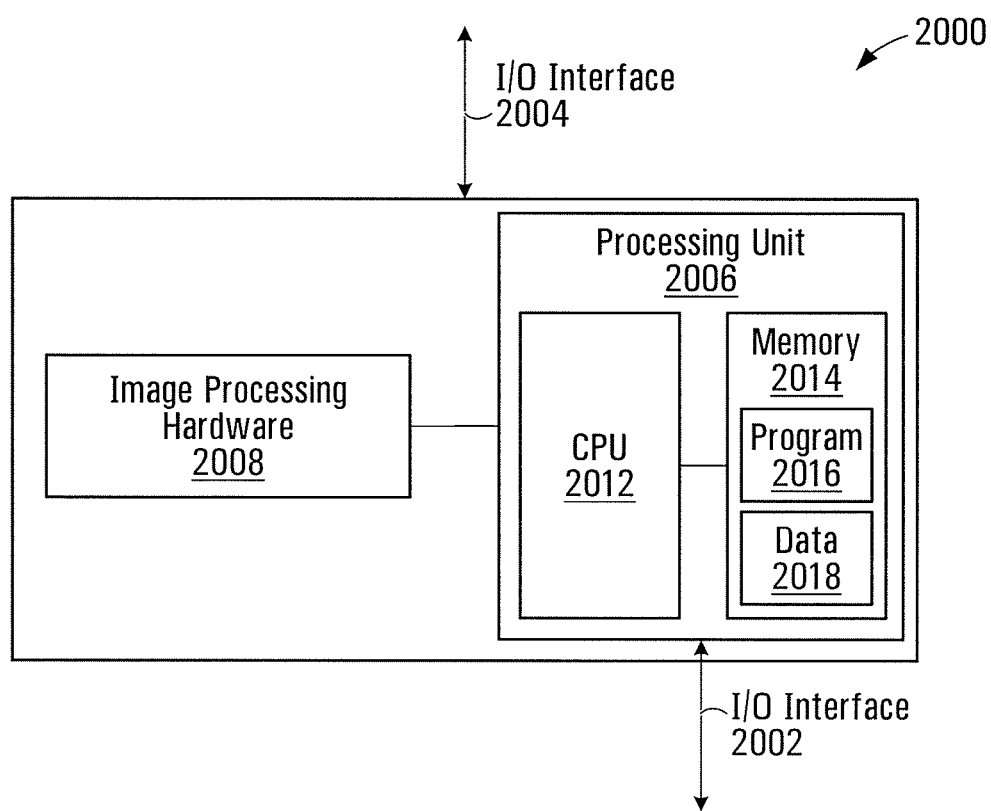
FIG. 20 is a block diagram of a computing apparatus suitable for use in connection with the apparatus illustrated in FIG. 3 in accordance with an alternative specific example of implementation of the invention.

Other alternative implementations of the processing module 112 can be implemented as a combination of dedicated hardware and software, of the type depicted in FIG. 20 and generally designated by reference numeral 2000. Such an implementation comprises a dedicated image processing hardware module 2008 and a general purpose computing unit 2006 including a CPU 2012 and a memory 2014 connected by a communication bus. The memory 2014 stores data 2018 and program instructions 2016. The CPU 2012 is adapted to process the data 2018 and the program instructions 2016 in order to implement the functions described in the specification and depicted in the drawings. As depicted, this specific implementation also comprise one or more I/O interfaces 2004, 2002 for receiving or sending data elements to external devices such as, for example, inspection and display devices of the type depicted in FIG. 1.

It will also be appreciated that the screening system 100 that is depicted in FIG. 1 may also be of a distributed nature where the X-ray images are obtained by an inspection device in one location (or more than one location) and then are transmitted over a network to another entity implementing the functionality of the processing module 112 described above. Another unit may then transmit a signal for causing one or more display devices to display information to the user, such as the X-ray image of the objects being scanned. The display device may be located in the same location where the X-ray images of objects were obtained or in an alternate location. In a non-limiting implementation, the display device may be part of a centralized screening facility.

Figure 21:
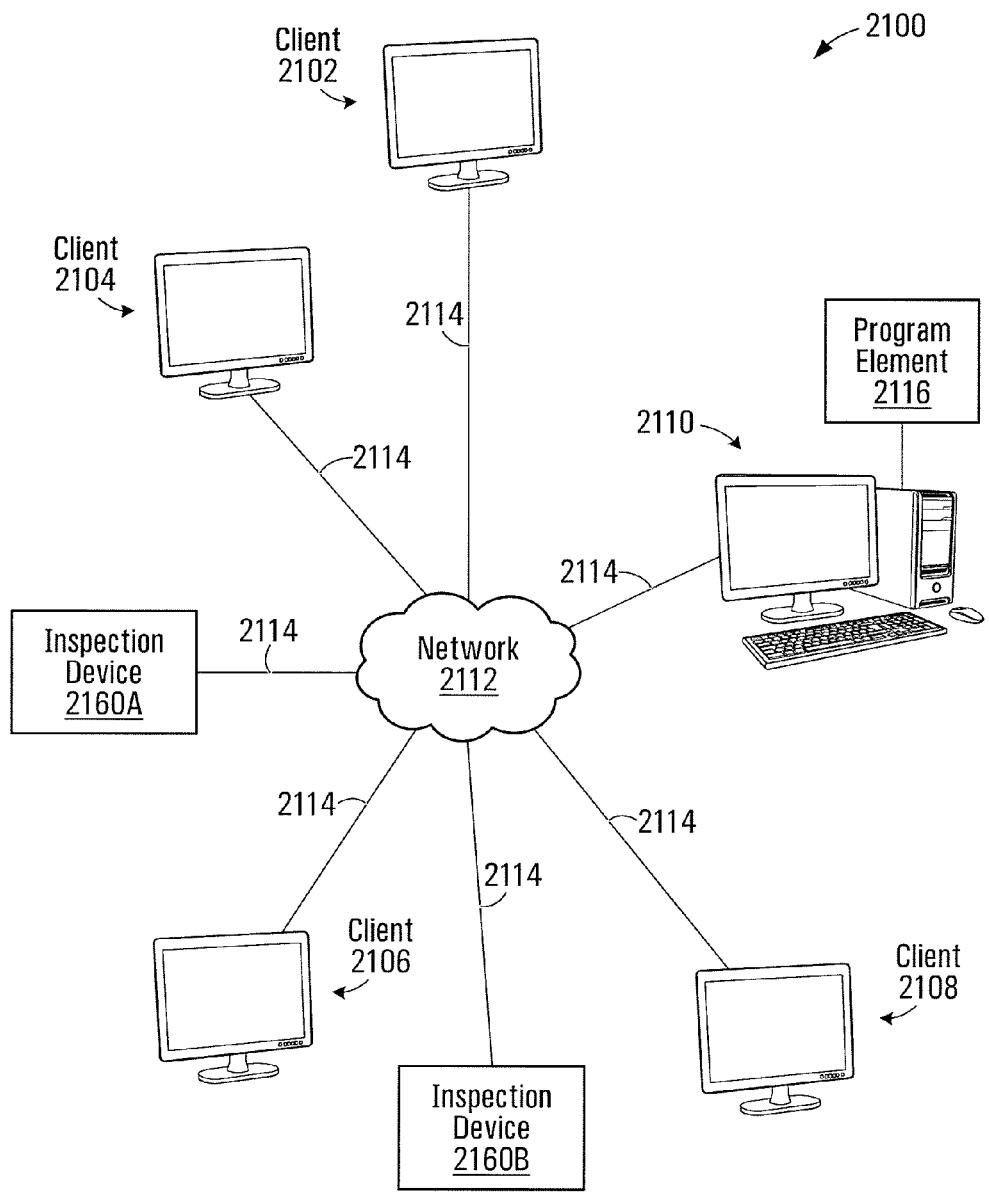
FIG. 21 shows a functional block diagram of a client-server system suitable for assessing a characteristic of a product at a security checkpoint in accordance with an alternative specific example of implementation of the present invention.

FIG. 21 illustrates a network-based client-server system 2100 for screening objects in accordance with a specific example of implementation of the invention. The client-server system 2100 includes a plurality of client systems 2102, 2104, 2106 and 2108, as well as inspection devices 2160A and 2160B connected to a server system 2110 through a network 2112. Communication links 2114 between the client systems 2102, 2104, 2106, 2108, the inspection devices 2160A, 2160B and the server system 2110 can be metallic conductors, optical fibers or wireless, without departing from the spirit of the invention. The network 2112 may be any suitable network including, but not limited to, a global public network such as the Internet, a private network and a wireless network. The server 2110 may be adapted to process information received from the inspection devices 2160A and 2160B and issue signals conveying screening results to the client systems 2102, 2104, 2106 and 2108 using suitable methods known in the computer-related arts.

The server system 2110 includes a program element 2116 for execution by a CPU (not shown). Program element 2116 includes functionality to implement the functionality of processing module 112 (shown in FIGS. 1 and 3) described above. Program element 2116 also includes the necessary networking functionality to allow the server system 2110 to communicate with the client systems 2102, 2104, 2106 and 2108, as well as the inspection devices 2160A and 2160B over the network 2112. In a specific implementation, the client systems 2102, 2104, 2106 and 2108 include display devices responsive to signals received from the server system 2110 for displaying screening results derived by the server system 2110.

Although the above embodiments have been described with reference to the inspection device 102 (shown in FIGS. 1 and 2), which embodied a single view X-ray imaging apparatus, it is to be appreciated that embodiments of the invention may be used in connection with any suitable type of inspection device, including a multi-view X-ray imaging apparatus.

As such, in an alternative example of implementation, the inspection device 102 is embodied as a multi-view X-ray machine. The multi-view X-ray machine generates X-ray image data associated with the liquid product conveying a first X-ray image of the liquid product taken by subjecting the liquid product to X-rays in a first orientation and a second X-ray image of the liquid product taken by subjecting the liquid product to X-rays in a second orientation. The first and second orientations are different from one another and will frequently be orthogonal to one another, although such differences in orientation may vary depending on the X-ray machine being used. In such an alternative implementation, the X-ray image data corresponding to the first X-ray image of the liquid product may be processed to derive information pertaining to the threat status of the liquid product according to the methods described above. The X-ray image data corresponding to the second X-ray image of the liquid product is then processed to validate and/or adjust the information derived based on the first X-ray image of the liquid product. Alternatively, the first and second X-ray image of the liquid product may be used jointly to derive shape information associated to a reference liquid product. For example, deriving shape information associated to a reference liquid product (see FIG. 4B, step 490 for example), an initial estimate of the shape information may be derived based on a first X-ray image of the liquid product. This initial estimate of the shape information may then be validated and/or refined by processing the second X-ray image of the liquid product to derive a second estimate of the shape information associated with the liquid product.

The person skilled in the art will appreciate that multiple images of a same product taken from different orientations may be used in an number of different manners in order to improve the assessment of the products under inspection.

For instance, an advantage of using a multi-view X-ray imaging apparatus, as compared to the use of a single view X-ray imaging apparatus, is that the additional view provides three-dimensional information that is otherwise unavailable from single two-dimensional view. Amongst others, these multiple views allow deriving a reference liquid product having characteristics that more closely approximate those of the liquid product under inspection.

It will also be appreciated that in alternate examples of implementations, the multi-view X-ray machine may generate X-ray image data conveying X-ray images of the liquid taken by subjecting the liquid product to X-rays in more than two orientations, thereby generating three, four or more X-ray images.

It will therefore be appreciated that other various modifications will become apparent to those skilled in the art and are within the scope of this invention, which is defined more particularly by the attached claims.

The invention claimed is:

1. A method for assessing a threat status of a liquid product under inspection at a security checkpoint, the liquid product being comprised of a bottle holding a liquid, wherein the bottle is at least partially filled with liquid, the method comprising:
   a) receiving X-ray image data associated with the liquid product under inspection, the X-ray image data being derived by performing an X-ray scan at the security checkpoint of the liquid product under inspection using an X-ray imaging apparatus, the X-ray image data conveying attenuation information resulting from interaction of X-rays with the liquid product;
   b) simulating a response of a reference liquid product to X-rays to generate simulated X-ray image data, wherein the reference liquid product is derived at least in part by processing the X-ray image data associated with the liquid product under inspection;
   c) comparing the simulated X-ray image data and the received X-ray image data to determine the threat status of the liquid product under inspection;
   d) releasing information conveying the determined threat status of the liquid product under inspection.

2. A method as defined in claim 1, wherein the reference liquid product is comprised of a reference bottle and a reference liquid.

3. A method as defined in claim 1, wherein said method comprises:
   a) deriving a virtual model of the reference liquid product; and
   b) using the virtual model of the reference liquid product in simulating the response of the reference liquid product to X-rays to generate the simulated X-ray image data.

4. A method as defined in claim 3, wherein the virtual model of the reference liquid product conveys 3-D geometric information associated with the reference liquid product.

5. A method as defined in claim 3, wherein the virtual model of the reference liquid product conveys location information associated with a meniscus formed by liquid.

6. A method as defined in claim 3, wherein deriving the virtual model of the reference liquid product comprises:
   a) generating a set of candidate virtual models;
   b) selecting at least one virtual model from the set of candidate virtual models at least in part by simulating responses to X-rays of the candidate virtual models in said set of candidate virtual models.

7. A method as defined in claim 6, wherein the candidate virtual models are generated at least in part by:
   a) processing the X-ray image data associated with the liquid product under inspection to derive geometric information associated with the liquid product;
   b) using the derived geometric information associated with the liquid product to generate the set of candidate virtual models.

8. A method as defined in claim 6, wherein generating the set of candidate virtual models includes generating virtual models of bottles having cross-sectional shapes selected from the set consisting of a generally circular shape, a generally elliptical shape, a generally rectangular shape and a generally square shape.

9. A method as defined in claim 6, wherein the set of candidate virtual models includes candidate virtual models associated with different levels of fill.

10. A method as defined in claim 6, wherein the set of candidate virtual models includes candidate virtual models associated to different liquid substances from a set of reference liquid substances.

11. A method as defined in claim 10, wherein the set of reference liquid substances includes at least one reference liquid substance that constitutes a threat.

12. A method as defined in claim 6, wherein selecting at least one virtual model from the set of candidate virtual models comprises:
   a) simulating responses to X-rays of the candidate virtual models in said set of candidate virtual models to obtain simulated X-ray data;
   b) effecting a comparison between the simulated X-ray data and the X-ray data associated to the liquid product under inspection;
   c) selecting the at least one virtual model from the set of candidate virtual models as the virtual model of the reference liquid product at least in part based on the comparison between the simulated X-ray data and the X-ray data associated to the liquid product under inspection.

13. A method as defined in claim 1, wherein the X-ray image data associated with the liquid product is obtained using a multi-view X-ray machine, said X-ray image data conveying a first X-ray image of the liquid product taken by subjecting the liquid product to X-rays in a first orientation and a second X-ray image of the liquid product taken by subjecting the liquid product to X-rays in a second orientation.

14. A method as defined in claim 13, wherein said method comprises:

a) deriving a virtual model of the reference liquid product based at least in part on the first X-ray image and the second X-ray image;
b) using the virtual model of the reference liquid product in simulating responses of the reference liquid product to X-rays in the first orientation to generate simulated X-ray image data.

15. A method as defined in claim 1, said method comprising:
a) placing the liquid product under inspection in a tray;
b) introducing the tray and the liquid product in a scanning area of the X-ray imaging apparatus.

16. A method as defined in claim 15, wherein the bottle holding the liquid has a top extremity and a bottom extremity, the method comprising positioning the bottle to induce a meniscus formed by the liquid in the bottle to migrate toward one of the extremities while performing the X-ray inspection of the liquid product.

17. A computer program product, tangibly stored on one or more non-transitory computer readable storage media, for assessing a threat status of a liquid product under inspection at a security checkpoint, the liquid product being comprised of a bottle holding a liquid, wherein the bottle is at least partially filled with liquid, the program product comprising instructions that, when executed, cause a programmable system including at least one programmable processor to perform operations, said operations comprising:
i) receiving X-ray image data associated with the liquid product under inspection, the X-ray image data being derived by performing an X-ray scan of the liquid product using an X-ray imaging apparatus, the X-ray image data conveying attenuation information resulting from interaction of X-rays with the liquid product under inspection;
ii) simulating a response of a reference liquid product to X-rays to generate simulated X-ray image data, wherein the reference liquid product is derived at least in part by processing the X-ray image data associated with the liquid product under inspection;
iii) comparing the simulated X-ray image data and the received X-ray image data to determine the threat status of the liquid product under inspection;
iv) releasing information conveying the determined threat status of the liquid product under inspection.

18. An apparatus for assessing a threat status of a liquid product under inspection at a security checkpoint, the liquid product being comprised of a bottle holding a liquid, wherein the bottle is at least partially filled with liquid, said apparatus comprising an input, a processing unit and an output, said apparatus comprising:
i) an input for receiving X-ray image data associated with the liquid product under inspection, the X-ray image data being derived by performing an X-ray scan of the liquid product under inspection using an X-ray imaging apparatus, the X-ray image data conveying attenuation information resulting from interaction of X-rays with the liquid product;
ii) a processor in communication with said input, said processor being programmed for:
(1) simulating a response of a reference liquid product to X-rays to generate simulated X-ray image data, wherein the reference liquid product is derived at least in part by processing the X-ray image data associated with the liquid product under inspection;
(2) comparing the simulated X-ray image data and the received X-ray image data to determine the threat status of the liquid product under inspection;
iii) an output for releasing information conveying the determined threat status of the liquid product under inspection.

19. A system suitable for assessing a threat status of a liquid product under inspection at a security checkpoint, the liquid product being comprised of a bottle holding a liquid, wherein the bottle is at least partially filled with liquid, said system comprising:
a) an inspection device for performing an X-ray inspection on the liquid product using penetrating radiation to generate X-ray image data associated with the liquid product under inspection;
b) an apparatus as defined in claim 18 for assessing the threat status of the liquid product under inspection;
c) a display screen in communication with the output of said apparatus for visually conveying to an operator the assessed threat status of the liquid product under inspection based on information released by the apparatus.

20. A system as defined in claim 19, wherein the inspection device is a multi-view X-ray machine.

21. A system as defined in claim 19, wherein the inspection device is a single-view X-ray machine.

22. A method for deriving a characteristic of a product under inspection using X-rays, the method comprising:
a) receiving X-ray image data associated with the product under inspection, the X-ray image data being derived by performing an X-ray scan of the product under inspection using an X-ray imaging apparatus, the X-ray image data conveying attenuation information resulting from interaction of X-rays with the product under inspection;
b) simulating a response of a reference product to X-rays to generate simulated X-ray image data, wherein the reference product is derived at least in part by processing the X-ray image data associated with the product under inspection;
c) comparing the simulated X-ray image data and the received X-ray image data to derive the characteristic of the product under inspection;
d) releasing information conveying the derived characteristic of the product under inspection.

23. A method as defined in claim 22, where the characteristic is selected from the set consisting of material density, type of material, threat status, linear attenuation coefficient and effective atomic number ($Z_{eff}$ number).

24. A method as defined in claim 22, said method comprising:
a) deriving a virtual model of the reference product; and
b) using the virtual model of the reference product in simulating the response of the reference product to X-rays to generate the simulated X-ray image data.

25. A method as defined in claim 24, wherein deriving the virtual model of the reference product comprises:
a) generating a set of candidate virtual models;
b) selecting at least one virtual model from the set of candidate virtual models at least in part by simulating responses to X-rays of the candidate virtual models in said set of candidate virtual models.

26. A method as defined in claim 25, wherein the candidate virtual models are generated at least in part by:
a) processing the X-ray image data associated with the product under inspection to derive geometric information associated with the product;
b) using the derived geometric information associated with the product to generate the set of candidate virtual models.

27. A method as defined in claim 25, wherein the set of candidate virtual models includes candidate virtual models associated to different substances from a set of reference substances.

28. A method as defined in claim 25, wherein selecting at least one virtual model from the set of candidate virtual models comprises:
   a) simulating responses to X-rays of the candidate virtual models in said set of candidate virtual models to obtain simulated X-ray data;
   b) effecting a comparison between the simulated X-ray data and the X-ray data associated to the product under inspection;
   c) selecting the at least one virtual model from the set of candidate virtual models as the virtual model of the reference product at least in part based on the comparison between the simulated X-ray data and the X-ray data associated to the product under inspection.

29. A method as defined in claim 22, wherein the X-ray image data associated with the product under inspection is obtained using a multi-view X-ray machine, said X-ray image data conveying a first X-ray image of the product under inspection taken by subjecting the product to X-rays in a first orientation and a second X-ray image of the product under inspection taken by subjecting the product to X-rays in a second orientation.

30. A method as defined in claim 29, wherein said method comprises:
   a) deriving a virtual model of the reference product based at least in part on the first X-ray image and the second X-ray image;
   b) using the virtual model of the reference product in simulating responses of the reference product to X-rays in the first orientation to generate simulated X-ray image data.

31. A computer program product, tangibly stored on one or more non-transitory computer readable storage media, for deriving a characteristic of a product under inspection based in part on an X-ray image of the product, the program product comprising instructions that, when executed, cause a programmable system including at least one programmable processor to perform operations, said operations comprising:
   i) receiving X-ray image data associated with the product under inspection, the X-ray image data being derived by performing an X-ray scan of the product using an X-ray imaging apparatus, the X-ray image data conveying attenuation information resulting from interaction of X-rays with the product under inspection;
   ii) simulating a response of a reference product to X-rays to generate simulated X-ray image data, wherein the reference product is derived at least in part by processing the X-ray image data associated with the product under inspection;
   iii) comparing the simulated X-ray image data and the received X-ray image data to derive the characteristic of the product under inspection;
   iv) releasing information conveying the derived characteristic of the product under inspection.

32. An apparatus as defined in claim 18, wherein the reference liquid product is comprised of a reference bottle and a reference liquid.

33. An apparatus as defined in claim 18, wherein said processor is programmed for:
   a) deriving a virtual model of the reference liquid product; and
   b) using the virtual model of the reference liquid product in simulating the response of the reference liquid product to X-rays to generate the simulated X-ray image data.

34. An apparatus as defined in claim 33, wherein the virtual model of the reference liquid product conveys 3-D geometric information associated with the reference liquid product.

35. An apparatus as defined in claim 33, wherein the virtual model of the reference liquid product conveys location information associated with a meniscus formed by liquid.

36. An apparatus as defined in claim 33, wherein deriving the virtual model of the reference liquid product comprises:
   a) generating a set of candidate virtual models;
   b) selecting at least one virtual model from the set of candidate virtual models at least in part by simulating responses to X-rays of the candidate virtual models in said set of candidate virtual models.

37. An apparatus as defined in claim 36, wherein the candidate virtual models are generated at least in part by:
   a) processing the X-ray image data associated with the liquid product under inspection to derive geometric information associated with the liquid product;
   b) using the derived geometric information associated with the liquid product to generate the set of candidate virtual models.

38. An apparatus as defined in claim 36, wherein generating the set of candidate virtual models includes generating virtual models of bottles having cross-sectional shapes selected from the set consisting of a generally circular shape, a generally elliptical shape, a generally rectangular shape and a generally square shape.

39. An apparatus as defined in claim 36, wherein the set of candidate virtual models includes candidate virtual models associated with different levels of fill.

40. An apparatus as defined in claim 36, wherein the set of candidate virtual models includes candidate virtual models associated to different liquid substances from a set of reference liquid substances.

41. An apparatus as defined in claim 40, wherein the set of reference liquid substances includes at least one reference liquid substance that constitutes a threat.

42. An apparatus as defined in claim 36, wherein selecting at least one virtual model from the set of candidate virtual models comprises:
   a) simulating responses to X-rays of the candidate virtual models in said set of candidate virtual models to obtain simulated X-ray data;
   b) effecting a comparison between the simulated X-ray data and the X-ray data associated to the liquid product under inspection;
   c) selecting the at least one virtual model from the set of candidate virtual models as the virtual model of the reference liquid product at least in part based on the comparison between the simulated X-ray data and the X-ray data associated to the liquid product under inspection.

43. A computer program product as defined in claim 31, wherein the reference liquid product is comprised of a reference bottle and a reference liquid.

44. A computer program product as defined in claim 31, wherein said operations comprise:
   a) deriving a virtual model of the reference liquid product; and
   b) using the virtual model of the reference liquid product in simulating the response of the reference liquid product to X-rays to generate the simulated X-ray image data.

45. A computer program product as defined in claim 44, wherein the virtual model of the reference liquid product conveys 3-D geometric information associated with the reference liquid product.

46. A computer program product as defined in claim 44, wherein the virtual model of the reference liquid product conveys location information associated with a meniscus formed by liquid.

47. A computer program product as defined in claim 44, wherein deriving the virtual model of the reference liquid product comprises:
 a) generating a set of candidate virtual models;
 b) selecting at least one virtual model from the set of candidate virtual models at least in part by simulating responses to X-rays of the candidate virtual models in said set of candidate virtual models.

48. A computer program product as defined in claim 47, wherein the candidate virtual models are generated at least in part by:
 a) processing the X-ray image data associated with the liquid product under inspection to derive geometric information associated with the liquid product;
 b) using the derived geometric information associated with the liquid product to generate the set of candidate virtual models.

49. A computer program product as defined in claim 47, wherein generating the set of candidate virtual models includes generating virtual models of bottles having cross-sectional shapes selected from the set consisting of a generally circular shape, a generally elliptical shape, a generally rectangular shape and a generally square shape.

50. A computer program product as defined in claim 47, wherein the set of candidate virtual models includes candidate virtual models associated with different levels of fill.

51. A computer program product as defined in claim 47, wherein the set of candidate virtual models includes candidate virtual models associated to different liquid substances from a set of reference liquid substances.

52. A computer program product as defined in claim 51, wherein the set of reference liquid substances includes at least one reference liquid substance that constitutes a threat.

53. A computer program product as defined in claim 47, wherein selecting at least one virtual model from the set of candidate virtual models comprises:
 a) simulating responses to X-rays of the candidate virtual models in said set of candidate virtual models to obtain simulated X-ray data;
 b) effecting a comparison between the simulated X-ray data and the X-ray data associated to the liquid product under inspection;
 c) selecting the at least one virtual model from the set of candidate virtual models as the virtual model of the reference liquid product at least in part based on the comparison between the simulated X-ray data and the X-ray data associated to the liquid product under inspection.

* * * * *